US008440694B2

(12) United States Patent
Turner et al.

(10) Patent No.: US 8,440,694 B2
(45) Date of Patent: May 14, 2013

(54) QUINOLINE COMPOUNDS SUITABLE FOR TREATING DISORDERS THAT RESPOND TO MODULATION OF THE SEROTONIN-5-HT$_6$ RECEPTOR

(75) Inventors: Sean Colm Turner, Ludwigshafen (DE); Wilfried Braje, Ludwigshafen (DE); Andreas Haupt, Ludwigshafen (DE); Udo Lange, Ludwigshafen (DE); Karla Drescher, Ludwigshafen (DE); Karsten Wicke, Ludwigshafen (DE); Liliane Unger, Ludwigshafen (DE); Mario Mezler, Ludwigshafen (DE); Matthias Mayrer, Ludwigshafen (DE); Wolfgang Wernet, Neustadt (DE); Andrea Hager-Wernet, legal representative, Neustadt (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 0 days.

(21) Appl. No.: 13/613,344

(22) Filed: Sep. 13, 2012

(65) Prior Publication Data

US 2013/0005703 A1 Jan. 3, 2013

Related U.S. Application Data

(62) Division of application No. 12/664,394, filed as application No. PCT/EP2008/060335 on Aug. 6, 2008, now Pat. No. 8,293,913.

(30) Foreign Application Priority Data

Aug. 7, 2007 (EP) ..................................... 07113962

(51) Int. Cl.
| | |
|---|---|
| A61K 31/47 | (2006.01) |
| A61P 3/04 | (2006.01) |
| A61P 25/00 | (2006.01) |
| A61P 25/18 | (2006.01) |
| A61P 25/28 | (2006.01) |
| A61P 25/30 | (2006.01) |
| C07D 215/36 | (2006.01) |

(52) U.S. Cl.
USPC .......................................... 514/312; 546/153

(58) Field of Classification Search ........................ None
See application file for complete search history.

(56) References Cited

U.S. PATENT DOCUMENTS

| | | |
|---|---|---|
| 2003/0130287 A1 | 7/2003 | Ackermann et al. |
| 2007/0027161 A1 | 2/2007 | Harris et al. |

FOREIGN PATENT DOCUMENTS

| | | |
|---|---|---|
| CA | 2237590 | 5/1997 |
| WO | 03080580 | 10/2003 |
| WO | WO03/080580 A2 * | 10/2003 |
| WO | 2005026125 | 3/2005 |
| WO | 2005113539 | 12/2005 |
| WO | 2006053785 | 5/2006 |
| WO | 2007039219 | 4/2007 |

OTHER PUBLICATIONS

Heal et al., Selective 5-HT6 receptor ligands: Progress in the development of a novel pharmacological approach to the treatment of obesity and related metabolic disorders, 117(2) Pharmacology & Therapeutics, 207-231 (2008).*
Sierksma et al., Major depression, cognitive dysfunction and Alzheimer's disease: Is there a link?, 626 EURO. J. Pharmacology 72-82 (2010).*
Poyurovsky et al., Effect of the 5-HT2 antagonist mianserin on cognitive dysfunction in chronic schizophrenia patients: an add-on, double-blind placebo-controlled study, 13 EURO. Neuropsychopharmacology 123-128 (2003).*
Martin, Y.C. et al., "Do structurally similar molecules have similar biological activity?" J. med. Chem. (2002) 45:4350-4358, 4536.
Shen et al., "Synthesis and structure-activity relationship of novel lactam-fused chroman derivatives having dual affinity at the 5-HT1A receptor and the serotonin transporter," Bioorg. Med. Chem. Lett. (2010) 20:222-227.
Notice of Allowance in U.S. Appl. No. 12/664,394 dated Jun. 11, 2012 (7 pages).
Office Action in U.S. Appl. No. 12/664,394 dated Aug. 31, 2011 (7 pages).
Office Action in U.S. Appl. No. 12/664,394 dated Mar. 7, 2011 (12 pages).

* cited by examiner

*Primary Examiner* — Janet Andres
*Assistant Examiner* — Timothy R. Rozof
(74) *Attorney, Agent, or Firm* — Lisa V. Mueller; Michael Best & Friedrich LLP

(57) ABSTRACT

The present invention relates to novel quinoline compounds of the formula (I) and to the salts thereof. The compounds possess valuable therapeutic properties and are particularly suitable, for treating diseases that respond to modulation of the serotonin 5-HT$_6$ receptor. In formula (I) R is a moiety of the formula (R) wherein * indicates the binding site to the quinolinyl radical and wherein A, B, X', Y, Q, $R^1$, $R^2$, $R^3$, $R^4$, $R^5$, m, n, p, q, $R^a$, $R^b$, X and Ar are as defined in claim 1.

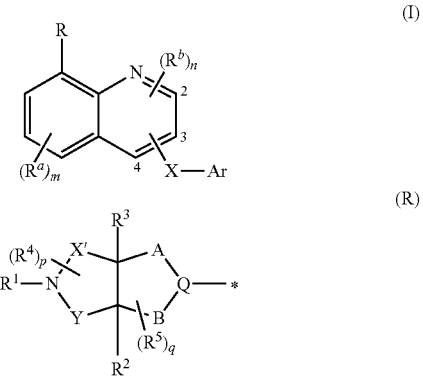

13 Claims, No Drawings

QUINOLINE COMPOUNDS SUITABLE FOR TREATING DISORDERS THAT RESPOND TO MODULATION OF THE SEROTONIN-5-HT$_6$ RECEPTOR

CROSS-REFERENCE TO RELATED APPLICATIONS

This is a divisional of U.S. patent application Ser. No. 12/664,394, filed Jul. 28, 2010, which is the U.S. national stage entry of International Patent Application No. PCT/EP2008/060335, filed on Aug. 6, 2008, which claims priority to European Patent Application No. 07113962.0, filed on Aug. 7, 2007, the contents of all of which are herein fully incorporated by reference.

BACKGROUND OF THE INVENTION

The present invention relates to novel quinoline compounds. The compounds possess valuable therapeutic properties and are particularly suitable, for treating diseases that respond to modulation of the serotonin 5-HT$_6$ receptor.

Serotonin (5-hydroxytryptamine, 5-HT), a monoamine neurotransmitter and local hormone, is formed by the hydroxylation and decarboxylation of tryptophan. The greatest concentration is found in the enterochromaffin cells of the gastrointestinal tract, the remainder being predominantly present in platelets and in the Central Nervous System (CNS). 5-HT is implicated in a vast array of physiological and pathophysiological pathways. In the periphery, it contracts a number of smooth muscles and induces endothelium-dependent vasodilation. In the CNS, it is believed to be involved in a wide range of functions, including the control of appetite, mood, anxiety, hallucinations, sleep, vomiting and pain perception.

Neurons that secrete 5-HT are termed serotonergic. The function of 5-HT is exerted upon its interaction with specific (serotonergic) neurons. Until now, seven types of 5-HT receptors have been identified: 5-HT$_1$ (with subtypes 5-HT$_{1A}$, 5-HT$_{1B}$, 5-HT$_{1D}$, 5-HT$_{1E}$ and 5-HT$_{1F}$), 5-HT$_2$ (with subtypes 5-HT$_{2A}$, 5-HT$_{2B}$ and 5-HT$_{2C}$), 5-HT$_3$, 5-HT$_4$, 5-HT$_5$ (with subtypes 5-HT$_{5A}$ and 5-HT$_{5B}$), 5-HT$_6$ and 5-HT$_7$. Most of these receptors are coupled to G-proteins that affect the activities of either adenylate cyclase or phospholipase Cγ.

The human 5-HT$_6$ receptors are positively coupled to adenylyl cyclase. They are distributed throughout the limbic, striatal and cortical regions of the brain and show a high affinity to antipsychotics.

The modulation of the 5-HT$_6$ receptor by suitable substances is expected to improve certain disorders including cognitive dysfunctions, such as a deficit in memory, cognition and learning, in particular associated with Alzheimer's disease, age-related cognitive decline and mild cognitive impairment, attention deficit disorder/hyperactivity syndrome, personality disorders, such as schizophrenia, in particular cognitive deficits related with schizophrenia, affective disorders such as depression, anxiety and obsessive compulsive disorders, motion or motor disorders such as Parkinson's disease and epilepsy, migraine, sleep disorders (including disturbances of the Circadian rhythm), feeding disorders, such as anorexia and bulimia, certain gastrointestinal disorders such as Irritable Bowel Syndrome, diseases associated with neurodegeneration, such as stroke, spinal or head trauma and head injuries, such as hydrocephalus, drug addiction and obesity.

Quinoline compounds having an affinity for the 5-HT$_6$ receptor have been described in the prior art, e.g. in US 2007/0027161, WO 2007/039219, WO 2006/053785, WO 05/026125, WO 05/113539 and WO 03/080580.

The compounds disclosed in US 2007/0027161, WO 05/026125 and WO 03/080580 carry an optionally substituted piperazin-1-yl radical or homopiperazin-1-yl radical in the 8-position of the quinoline moiety.

The compounds disclosed in WO 05/113539 carry an amino-substituted piperidin-1-yl radical or pyrrolidin-1-yl radical in the 8-position of the quinoline moiety.

The compounds disclosed in WO 05/113539 carry an aminomethyl or aminoethyl radical in the 8-position of the quinoline moiety.

However, there is still an ongoing need for providing compounds having high affinity for the 5-HT$_6$ receptor and which show high selectivity to this receptor. In particular the compounds should have low affinity to adrenergic receptors, such as α$_1$-adrenergic receptor, histamine receptors, such as H$_1$-receptor, and dopaminergic receptors, such as D$_2$-receptor, in order to avoid or reduce considerable side effects associated with modulation of these receptors, such as postural hypotension, reflex tachycardia, potentiation of the antihypertensive effect of prazosin, terazosin, doxazosin and labetalol or dizziness associated to the blockade of the α$_1$-adrenergic receptor, weight gain, sedation, drowsiness or potentiation of central depressant drugs associated to the blockade of the H$_1$-receptor, or extrapyramidal movement disorder, such as dystonia, parkinsonism, akathisia, tardive dyskinesia or rabbit syndrome, or endocrine effects, such as prolactin elevation (galactorrhea, gynecomastia, menstruyl changes, sexual dysfunction in males), associated to the blockade of the D$_2$-receptor.

It is an object of the present invention to provide compounds which have a high affinity and selectivity for the 5-HT$_6$ receptor, thus allowing the treatment of disorders related to or affected by the 5-HT$_6$ receptor.

The compounds should also have good pharmacological profile, e.g. a good brain plasma ratio, a good bioavailability, good metabolic stability, or a decreased inhibition of the mitochondrial respiration.

SUMMARY OF THE INVENTION

It has now been found that the quinoline compounds of the formula (I) as defined herein, their physiologically tolerated acid addition salts and the N-oxides thereof exhibit to a surprising and unexpected degree, selective binding to the 5-HT$_6$ receptor. Therefore, the present invention relates to the compounds of formula (I)

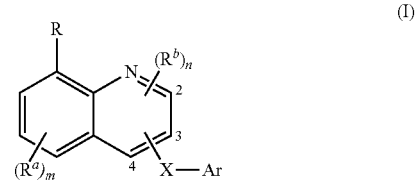

(I)

wherein
R is a moiety of the formula

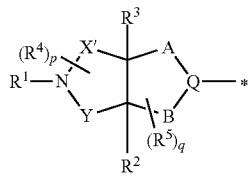

wherein * indicates the binding site to the quinolinyl radical;
A is $(CH_2)_a$ with a being 0, 1, 2 or 3;
B is $(CH_2)_b$ with b being 0, 1, 2 or 3;
X' is $(CH_2)_x$ with x being 0, 1, 2 or 3;
Y is $(CH_2)_y$ with y being 0, 1, 2 or 3;
provided that a+b is 1, 2, 3 or 4, x+y is 1, 2, 3 or 4 and a+b+x+y is 3, 4, 5, 6 or 7;
Q is N or CH;
$R^1$ is hydrogen, $C_1$-$C_6$-alkyl, $C_1$-$C_6$-hydroxyalkyl, $C_1$-$C_6$-haloalkyl, $C_1$-$C_6$-alkoxy-$C_1$-$C_4$-alkyl, $C_3$-$C_6$-cycloalkyl, $C_3$-$C_6$-halocycloalkyl, $C_3$-$C_6$-cycloalkyl-$C_1$-$C_4$-alkyl, hetaryl-$C_1$-$C_4$-alkyl, $C_3$-$C_6$-alkenyl, $C_3$-$C_6$-haloalkenyl, formyl, $C_1$-$C_4$-alkylcarbonyl, $C_1$-$C_4$-alkoxycarbonyl, phenoxycarbonyl or benzyloxycarbonyl, where the phenyl rings in the last two mentioned moieties are unsubstituted or carry 1, 2 or 3 substituents, selected from halogen, $C_1$-$C_4$-alkyl or $C_1$-$C_4$-haloalkyl, in particular hydrogen, $C_1$-$C_6$-alkyl, $C_1$-$C_6$-hydroxyalkyl, $C_1$-$C_6$-haloalkyl, $C_1$-$C_6$-alkoxy-$C_1$-$C_4$-alkyl, $C_1$-$C_6$-haloalkoxy-$C_1$-$C_4$-alkyl, $C_3$-$C_6$-cycloalkyl, $C_3$-$C_6$-halocycloalkyl, $C_3$-$C_6$-cycloalkyl-$C_1$-$C_4$-alkyl, hetaryl-$C_1$-$C_4$-alkyl, $C_3$-$C_6$-alkenyl, $C_3$-$C_6$-haloalkenyl, formyl, $C_1$-$C_4$-alkylcarbonyl or $C_1$-$C_4$alkoxycarbonyl;
$R^2$ is hydrogen, $C_1$-$C_4$-alkyl or $C_1$-$C_4$-haloalkyl;
$R^3$ is hydrogen, $C_1$-$C_4$-alkyl or $C_1$-$C_4$-haloalkyl;
p is 0, 1 or 2;
q is 0, 1 or 2;
$R^4$ if present, is $C_1$-$C_4$-alkyl or $C_1$-$C_4$-haloalkyl and bound to X and/or Y, or,
  if p is 1 or 2, one radical $R^4$, which is bound to a carbon atom of X or Y adjacent to the nitrogen atom, together with $R^1$ may also be linear $C_2$-$C_5$-alkylene, which may carry 1 or 2 radicals $R^6$; or,
  if p is 2, two radicals $R^4$, which are bound to adjacent carbon atoms of X or Y together may also be linear $C_2$-$C_5$-alkylene, which may carry 1 or 2 radicals $R^6$;
$R^5$ if present, is $C_1$-$C_4$alkyl or $C_1$-$C_4$-haloalkyl and bound to A and/or B;
$R^6$ is $C_1$-$C_4$-alkyl, $C_1$-$C_4$-alkoxy or $C_1$-$C_4$-haloalkoxy;
n is 0, 1 or 2;
m is 0, 1, 2 or 3;
$R^a$, $R^b$ are independently selected from the group consisting of halogen, CN, $C_1$-$C_4$-alkyl, $C_1$-$C_4$-haloalkyl, $C_1$-$C_4$-alkoxy, $C_1$-$C_4$-haloalkoxy, $C(O)R^{aa}$, $C(O) NR^{cc}R^{bb}$ and $NR^{cc}R^{bb}$;
  wherein $R^{aa}$ is hydrogen, $C_1$-$C_4$-alkyl, $C_1$-$C_4$-haloalkyl, $C_1$-$C_4$-alkoxy or $C_1$-$C_4$-haloalkoxy, and
  $R^{cc}$, $R^{bb}$ are independently selected from the group consisting of hydrogen and $C_1$-$C_4$-alkyl;
X is $CH_2$, $C(O)$, S, $S(O)$ or $S(O)_2$; which is located in the 3- or 4-position of the quinoline ring;

Ar is a radical $Ar^1$, $Ar^2$—$Ar^3$ or $Ar^2$—O—$Ar^3$, wherein $Ar^1$, $Ar^2$ and $Ar^3$ are each independently selected from the group consisting of aryl or hetaryl wherein aryl or hetaryl moieties may be unsubstituted or may carry 1, 2, 3 substituents $R^x$, wherein
  $R^x$ is halogen, CN, $NO_2$, $C_1$-$C_6$-haloalkyl, $C_1$-$C_6$-hydroxyalkyl, $C_1$-$C_6$-alkoxy-$C_1$-$C_4$-alkyl, $C_2$-$C_6$-alkenyl, $C_2$-$C_6$-haloalkenyl, $C_3$-$C_6$-cycloalkyl, $C_3$-$C_6$-halocycloalkyl, $C_1$-$C_6$-alkoxy, $C_1$-$C_6$-hydroxyalkoxy, $C_1$-$C_6$-alkoxy-$C_1$-$C_4$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_1$-$C_6$-alkylcarbonyl, $C_1$-$C_6$-haloalkylcarbonyl, $C_1$-$C_6$-alkylcarbonylamino, $C_1$-$C_6$-haloalkylcarbonylamino, carboxy, NH—C(O)—$NR^{x1}R^{x2}$, $NR^{x1}R^{x2}$, $NR^{x1}R^{x2}$—$C_1$-$C_6$-alkylene, O—$NR^{x1}R^{x2}$, wherein $R^{x1}$ and $R^{x2}$ in the last 4 mentioned radicals are independently of each other hydrogen, $C_1$-$C_6$-alkyl, $C_1$-$C_6$-haloalkyl or $C_1$-$C_6$-alkoxy or $R^{x1}$ and $R^{x2}$ in the last 4 mentioned radicals together with the nitrogen atom form an N-bound 5-, 6- or 7-membered, saturated heterocycle or an N-bound 7-, 8-, 9- or 10-membered, saturated heterobicycle which are unsubstituted or which carry 1, 2, 3 or 4 radicals selected from $C_1$-$C_4$-alkyl, $C_1$-$C_4$-haloalkyl, $C_1$-$C_4$-hydroxyalkyl and $C_1$-$C_4$-alkoxy and wherein 2 radicals $R^x$, which are bound to adjacent carbon atoms of Ar may form a saturated or unsaturated 5- or 6-membered carbocyclic or heterocyclic ring, which itself may carry a radical $R^x$;
and physiologically tolerated acid addition salts and the N-oxides thereof.

The present invention also relates to a pharmaceutical composition which comprises at least one quinoline compound of the formula (I) and/or at least one physiologically tolerated acid addition salt of (I) and/or at least one N-oxide of (I), where appropriate together with physiologically acceptable carriers and/or auxiliary substances.

The present invention further relates to the use of a quinoline compound of the formula (I) and/or physiologically tolerated acid addition salts thereof and/or at least one N-oxide of (I), for preparing a pharmaceutical composition, optionally together with at least one physiologically acceptable carrier or auxiliary substance.

The compounds of the present invention (i.e. the quinoline compounds of the formula (I) the physiologically tolerated acid addition salts of (I), the N-oxides of (I) and the physiologically tolerated acid addition salts thereof) are selective 5-$HT_6$ receptor ligands. Thus the compounds of the present invention are particularly suitable as a medicament, in particular for the treatment of disorders of the central nervous system, addiction diseases or obesity, as these disorders and diseases are likely to respond to influencing by 5-$HT_6$ receptor ligands. Therefore the present invention also provides a method for treating disorders in mammals, said method comprising administering an effective amount of at least one compound of the formula (I) and/or at least one physiologically tolerated acid addition salt of (I) and/or at least one N-oxide of (I) to a subject in need thereof.

The invention also relates to the use of the compounds of the presention invention as a medicament, in particular a medicament for the treatment of a medical disorder as defined herein and in the claims.

DETAILED DESCRIPTION OF THE INVENTION

The diseases which are susceptible to treatment with a compound of the present invention include, e.g., disorders and diseases of the central nervous system, in particular cognitive dysfunctions, such as a deficit in memory, cognition and learning, in particular associated with Alzheimer's disease, age-related cognitive decline and mild cognitive impairment, attention deficit disorder/hyperactivity syndrome (ADHD), personality disorders, such as schizophrenia, in particular cognitive deficits related with schizophrenia, affective disorders such as depression, anxiety and obsessive compulsive disorders, motion or motor disorders such as Parkinson's disease and epilepsy, migraine, sleep disorders (including disturbances of the Circadian rhythm), feeding disorders, such as anorexia and bulimia, certain gastrointestinal disorders such as Irritable Bowel Syndrome, diseases associated with neurodegeneration, such as stroke, spinal or head trauma and head injuries, such as hydrocephalus, drug addiction and obesity.

According to the invention, at least one compound of the present invention, i.e. a quinoline compound of the general formula (I) having the meanings mentioned at the outset, a physiologically tolerated acid addition salt of (I), an N-oxide of (I) or a physiologically tolerated acid addition salt thereof is used for treating the above mentioned indications. Provided the compounds of the formula (I) of a given constitution may exist in different spatial arrangements, for example if they possess one or more centers of asymmetry, polysubstituted rings or double bonds, or as different tautomers, it is also possible to use enantiomeric mixtures, in particular racemates, diastereomeric mixtures and tautomeric mixtures, preferably, however, the respective essentially pure enantiomers, diastereomers and tautomers of the compounds of formula (I) and/or of their salts and/or their N-oxides.

It is likewise possible to use physiologically tolerated salts of the compounds of the formula (I), especially acid addition salts with physiologically tolerated acids. Examples of suitable physiologically tolerated organic and inorganic acids are hydrochloric acid, hydrobromic acid, phosphoric acid, sulfuric acid, $C_1$-$C_4$-alkylsulfonic acids, such as methanesulfonic acid, aromatic sulfonic acids, such as benzenesulfonic acid and toluenesulfonic acid, oxalic acid, maleic acid, fumaric acid, lactic acid, tartaric acid, adipic acid and benzoic acid. Other utilizable acids are described in Fortschritte der Arzneimittelforschung [Advances in drug research], Volume 10, pages 224 ff., Birkhäuser Verlag, Basel and Stuttgart, 1966.

It is likewise possible to use N-oxides of the compounds of the formula (I), if those compounds contain a basic nitrogen atom, such as the nitrogen atom of the quinoline moiety.

The compounds of the present invention can also be radio-labelled by incorporation of at least one radionucleide such as $^3$H, $^{11}$C, $^{13}$N, $^{15}$O, $^{18}$F, $^{75}$Br, $^{76}$Br, $^{77}$Br, $^{82}$Br, $^{123}$I, $^{125}$I and/or $^{131}$I. The incorporation of at least one radionucleide can be achieved by standard methods for incorporating radionucleides, e.g. by analogy to WO 2006/053785. Radiolabelled compounds of the present invention can be used e.g. for labelling 5-HT$_6$ receptors and for diagnostic imaging of 5-HT$_6$ receptors in mammals, in particular in humans. Radio-labelled compounds of the present invention can be used for diagnostic imaging of tissue expressing the 5-HT$_6$ receptors in mammals, in particular for diagnostic imaging of the brain.

Particular embodiments of radiolabelled compounds of the present invention relate to those compounds of the formula I, which include at least one positron emitting radionucleide such as $^{11}$C, $^{13}$N, $^{15}$O or $^{18}$F, in particular a radionucleide selected from $^{11}$C and $^{18}$F. Particular preferred embodiments of radiolabelled compounds of the present invention are those, wherein $R^1$ is $^{11}$C-methyl or Ar is $^{18}$F-substituted phenyl. Radiolabelled compounds of the present invention, which include at least one positron emitting radionucleide, are particularly useful for the labelling and diagnostic imaging of the 5-HT$_6$ receptor functionality by means of positron emission tomography (PET). These compounds are also particularly useful for the diagnostic imaging of tissue expressing the 5-HT$_6$ receptors in mammals, in particular for diagnostic imaging of the brain by means of PET. PET can be performed e.g. by analogy to the methods described in WO 2006/053785.

The organic moieties mentioned in the above definitions of the variables are—like the term halogen—collective terms for individual listings of the individual group members. The prefix $C_n$-$C_m$ indicates in each case the possible number of carbon atoms in the group.

The term "halogen" denotes in each case fluorine, bromine, chlorine or iodine, in particular fluorine, chlorine or bromine.

The term "$C_1$-$C_6$-alkyl" as used herein and in the alkyl moieties of $C_1$-$C_6$-hydroxyalkyl, $C_1$-$C_6$-alkoxy-$C_1$-$C_4$-alkyl, $C_1$-$C_6$-alkylthio, $C_1$-$C_6$-alkylsulfinyl, $C_1$-$C_6$-alkylsulfonyl, $C_1$-$C_6$-alkylcarbonyl, $C_1$-$C_6$-alkylcarbonylamino, $C_3$-$C_6$-cycloalkyl-$C_1$-$C_4$-alkyl, aryl-$C_1$-$C_4$-alkyl or hetaryl-$C_1$-$C_4$-alkyl denotes in each case a straight-chain or branched alkyl group having from 1 to 6 carbon atoms, preferably 1 to 4 carbon atoms. Examples of an alkyl group are methyl, ethyl, n-propyl, iso-propyl, n-butyl, 2-butyl, iso-butyl, tert-butyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

The term "$C_1$-$C_6$-haloalkyl" as used herein and in the haloalkyl moieties of $C_1$-$C_6$-haloalkylthio, $C_1$-$C_6$-haloalkylsulfinyl, $C_1$-$C_6$-haloalkylsulfonyl, $C_1$-$C_6$-haloalkylcarbonyl, $C_1$-$C_6$-haloalkylcarbonylamino denotes in each case a straight-chain or branched alkyl group having from 1 to 6 carbon atoms, wherein the hydrogen atoms of this group are partially or totally replaced with halogen atoms. Preferred haloalkyl moieties are selected from $C_1$-$C_4$-haloalkyl, especially preferred from $C_1$-$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluorethyl, 2,2,2-trichloroethyl, pentafluoroethyl and the like.

The term "$C_1$-$C_4$-alkylene" as used herein denotes a straight-chain or branched bivalent alkandiyl group having from 1 to 4 carbon atoms, examples including methylene, 1,1-ethylene (1,1-ethandiyl), 1,2-ethylene (1,2-ethandiyl), 1,1-propandiyl, 1,2-propandiyl, 2,2-propandiyl, 1,3-propandiyl, 1,1-butandiyl, 1,2-butandiyl, 1,3-butandiyl, 1,4-butandiyl, 2,3-butandiyl, 2,2-butanediyl. The term "linear $C_1$-$C_4$-alkylene" as used herein denotes a straight-chain bivalent alkandiyl group having from 1 to 4 carbon atoms, examples including methylene, 1,2-ethylene, 1,3-propandiyl and 1,4-butandiyl.

The term "$C_1$-$C_6$-alkoxy" as used herein and in the alkoxy moieties of $C_1$-$C_6$-alkoxy-$C_1$-$C_4$-alkyl denotes in each case a straight-chain or branched alkoxy group having from 1 to 6 carbon atoms, preferably 1 to 4 carbon atoms. Examples of an alkoxy group are methoxy, ethoxy, n-propoxy, iso-propoxy, n-butyloxy, 2-butyloxy, iso-butyloxy, tert-butyloxy, pentyloxy, 1-methylbutyloxy, 2-methylbutyloxy, 3-methylbutyloxy, 2,2-dimethylpropyloxy, 1-ethylpropyloxy, hexyloxy, 1,1-dimethylpropyloxy, 1,2-dimethylpropyloxy, 1-methylpentyloyx, 2-methylpentyloxy, 3-methylpentyloxy, 4-methylpentyloxy, 1,1-dimethylbutyloyx, 1,2-dimethylbutyloxy, 1,3-dimethylbutyloxy, 2,2-dimethylbutyloxy, 2,3-dimethylbutyloyx, 3,3-dimethylbutyloxy, 1-ethylbutyloxy, 2-ethylbutyloxy, 1,1,2-trimethylpropyloxy, 1,2,2-trimethylpropyloxy, 1-ethyl-1-methylpropyloxy and 1-ethyl-2-methylpropyloxy.

The term "$C_1$-$C_6$-haloalkoxy" as used herein and in the haloalkoxy moieties of $C_1$-$C_6$-haloalkoxy-$C_1$-$C_4$-alkyl denotes in each case a straight-chain or branched alkoxy group having from 1 to 6 carbon atoms, wherein the hydrogen atoms of this group are partially or totally replaced with halogen atoms, in particular fluorine atoms. Preferred haloalkoxy moieties include $C_1$-$C_4$-haloalkoxy, in particular $C_1$-$C_2$-fluoroalkoxy, such as fluoromethoxy, difluoromethoxy, trifluoromethoxy, 1-fluoroethoxy, 2-fluoroethoyx, 2,2-difluoroethoyx, 2,2,2-trifluoroethoxy, 2-chloro-2-fluoroethoxy, 2-chloro-2,2-difluoroethoxy, 2,2-dichloro-2-fluorethoxy, 2,2,2-trichloroethoxy, pentafluoroethoxy and the like.

The term "$C_1$-$C_6$-hydroxyalkyl" is a straight-chain or branched alkyl group having from 1 to 6, especially 1 to 4 carbon atoms (=$C_1$-$C_4$ hydroxyalkyl), in particular 1 to 3 carbon atoms (=$C_1$-$C_3$ hydroxyalkyl), wherein one of the hydrogen atoms is replaced by a hydroxy group, such as in 2-hydroxyethyl or 3-hydroxypropyl.

The term "$C_1$-$C_6$-alkoxy-$C_1$-$C_4$-alkyl" is a straight-chain or branched alkyl group having from 1 to 4 carbon atoms, wherein one of the hydrogen atoms is replaced by a $C_1$-$C_6$-alkoxy group, such as in methoxymethyl, ethoxymethyl, propoxymethyl, 1-methoxyethyl, 1-ethoxyethyl, 2-methoxyethyl, 2-ethoxyethyl, 2-methoxypropyl, 2-ethoxypropyl, 3-methoxypropyl or 3-ethoxypropyl.

The term "$C_1$-$C_6$-haloalkoxy-$C_1$-$C_4$-alkyl" is a straight-chain or branched alkyl group having from 1 to 4 carbon atoms, wherein one of the hydrogen atoms is replaced by a $C_1$-$C_6$-haloalkoxy group.

The term "$C_3$-$C_6$-cycloalkyl" as used herein and in the cycloalkyl moieties of $C_3$-$C_6$-cycloalkyl-$C_1$-$C_4$-alkyl and $C_3$-$C_6$-halocycloylkyl denotes in each case a cycloaliphatic radical having from 3 to 6 C atoms, such as cyclopropyl, cyclobutyl, cyclopentyl and cyclohexyl. The cycloalkyl radical may be unsubstituted or may carry 1, 2, 3 or 4 $C_1$-$C_4$-alkyl radicals, preferably a methyl radical.

The term "$C_3$-$C_6$-halocycloalkyl" as used herein and in the halocycloalkyl moieties of $C_3$-$C_6$-halocycloalkyl-$C_1$-$C_4$-alkyl denotes in each case a cycloaliphatic radical having from 3 to 6 C atoms, such as cyclopropyl, cyclobutyl, cyclopentyl and cyclohexyl, wherein at least one hydrogen radical, e.g. 1, 2, 3, 4 or 5 hydrogen radicals are replaced by halogen, in particular fluorine. Examples include 1-fluorocyclopropyl, 2-fluorocyclopropyl, 2,2-difluorocyclopropyl, 1-fluorocyclobutyl, 2-fluorocyclobutyl, 2,2-difluorocyclobutyl, 3-fluorocyclobutyl, 3,3-difluorocyclobutyl, 1,3-difluorocyclobutyl etc, The term "$C_2$-$C_6$-alkenyl" as used herein and in the alkenyl moieties of $C_3$-$C_6$-haloalkenyl and aryl-$C_2$-$C_4$-alkenyl denotes in each case a singly unsaturated hydrocarbon radical having 2, 3, 4, 5 or 6 C-atoms, e.g. vinyl, allyl (2-propen-1-yl), 1-propen-1-yl, 2-propen-2-yl, methallyl (2-methylprop-2-en-1-yl), 2-buten-1-yl, 3-buten-1-yl, 2-penten-1-yl, 3-penten-1-yl, 4-penten-1-yl, 1-methylbut-2-en-1-yl, 2-ethylprop-2-en-1-yl and the like.

The term "aryl" as used herein denotes in each case a carbocyclic radical selected from the group consisting of phenyl and phenyl fused to a saturated or unsaturated 5- or 6-membered carbocyclic ring, such as naphthyl, 1,2-dihydronaphtyl, 1,2,3,4-tetrahydronaphtyl, indenyl or indanyl, provided that in the fused rings aryl is bound via the phenyl part of the fused rings.

The term "hetaryl" as used herein denotes in each case a heterocyclic radical selected from the group consisting of monocyclic 5- or 6-membered heteroaromatic radicals comprising as ring members 1, 2 or 3 heteroatoms selected from N, O and S and 5- or 6-membered heteroaromatic ring fused to a phenyl ring or to a 5- or 6-membered heteroaromatic radical, where the heterocyclic ring comprises as ring members 1, 2 or 3 heteroatoms selected from N, O and S.

Examples of 5- or 6-membered heteroaromatic radicals include pyridyl, i.e. 2-, 3-, or 4-pyridyl, pyrimidinyl, i.e. 2-, 4- or 5-pyrimidinyl, pyrazinyl, pyridazinyl, i.e. 3- or 4-pyridazinyl, thienyl, i.e. 2- or 3-thienyl, furyl, i.e. 2- or 3-furyl, pyrrolyl, i.e. 2- or 3-pyrrolyl, oxazolyl, i.e. 2-, 3- or 5-oxazolyl, isoxazolyl, i.e. 3-, 4- or 5-isoxazolyl, thiazolyl, i.e. 2-, 3- or 5-thiazolyl, isothiazolyl, i.e. 3-, 4- or 5-isothiazolyl, pyrazolyl, i.e. 1-, 3-, 4- or 5-pyrazolyl, i.e. 1-, 2-, 4- or 5-imidazolyl, oxadiazolyl, e.g. 2- or 5-[1,3,4]oxadiazolyl, 4- or 5-(1, 2,3-oxadiazol)yl, 3- or 5-(1,2,4-oxadiazol)yl, 2- or 5-(1,3,4-thiadiazol)yl, thiadiazolyl, e.g. 2- or 5-(1,3,4-thiadiazol)yl, 4- or 5-(1,2,3-thiadiazol)yl, 3- or 5-(1,2,4-thiadiazol)yl, triazolyl, e.g. 1H-, 2H- or 3H-1,2,3-triazol-4-yl, 2H-triazol-3-yl, 1H-, 2H-, or 4H-1,2,4-triazolyl and tetrazolyl, i.e. 1H- or 2H-tetrazolyl.

Examples of a 5- or 6-membered heteroaromatic ring fused to a phenyl ring or to a 5- or 6-membered heteroaromatic radical include benzofuranyl, benzothienyl, indolyl, indazolyl, benzimidazolyl, benzoxathiazolyl, benzoxadiazolyl, benzothiadiazolyl, benzoxazinyl, chinolinyl, isochinolinyl, purinyl, 1,8-naphthyridyl, pteridyl, pyrido[3,2-d]pyrimidyl or pyridoimidazolyl and the like. These fused hetaryl radicals may be bonded to the remainder of the molecule (more precisely to the X group) via any ring atom of 5- or 6-membered heteroaromatic ring or via a carbon atom of the fused phenyl moiety.

Examples of rings Ar, wherein 2 radicals $R^x$, which are bound to adjacent carbon atoms of Ar, form a saturated or unsaturated 5- or 6-membered carbocyclic or heterocyclic ring include 2,3-dihydrobenzofuranyl, 2,3-dihydroindolyl, dihydroisoindolyl, dihydrobenzoxazinyl, tetrahydroisochinolinyl, benzomorpholinyl, chromenyl, chromanyl, 1,2-dihydronaphtyl, 1,2,3,4-tetrahydronaphtyl, indenyl and indanyl.

The term "saturated or unsaturated heterocyclic ring" in each case denotes a 3- to 7 membered cyclic radical containing at least one hetero atom selected from the group consisting of N, O and S. Examples for such saturated or unsaturated 3- to 7-membered heterocyclic rings comprise saturated or unsaturated, aromatic or non-aromatic heterocyclic rings. Examples therefore include, apart from the above-defined 5- or 6-membered heteroaromatic radicals, aziridyl, diaziridinyl, oxiranyl, azetidinyl, azetinyl, di- and tetrahydrofuranyl, pyrrolinyl, pyrrolidinyl, oxopyrrolidinyl, pyrazolinyl, pyrazolidinyl, imidazolinyl, imidazolidinyl, oxazolinyl, oxazolidinyl, oxo-oxazolidinyl, isoxazolinyl, isoxazolidinyl, piperidinyl, piperazinyl, morpholinyl, thiomorpholinyl, oxothiomorpholinyl, dioxothiomorpholinyl and the like.

N-bound 5-, 6- or 7-membered saturated heterocycles are generally saturated heteromonocyclic radicals containing one nitrogen atom as a ring member, which is attached to the remainder of the molecule, and optionally one or more, e.g. 1 or 2 further heteroatoms such as O, S or N as ring member, having a total of 5, 6 or 7 ring member atoms. Examples for "N-bound 5- to 7-membered saturated heterocycle" are pyrolidin-1-yl, piperidin-1-yl, piperazin-1-yl, 4-methylpiperazin-1-yl, morpholin-4-yl, thiomorpholin-4-yl, imidazolidin- 1-yl, oxazolidin-3-yl, thiazolidin-3-yl or hexahydrodiazepin-1-yl, especially pyrrolidin-1-yl, piperazin-1-yl, 4-methylpiperazin-1-yl, piperidin-1-yl and morpholin-4-yl.

N-bound 7- to 10-membered saturated heterobicycles are generally saturated heterobicycles containing one nitrogen atom as a ring member, which is attached to the remainder of the molecule, and optionally one or more, e.g. 1 or 2 further heteroatoms such as O, S or N as ring member, having a total of 7, 8, 9 or 10 ring member atoms. Examples of N-bound 7- to 10-membered saturated heterobicyclic radicals are the radicals R with Q being N and a+b+x+y being 3, 4, 5 or 6.

With regard to their ability to bind to the 5-HT$_6$ receptor preference is given to compounds of formula (I), wherein the variables Ar, A, X, n, m, $R^1$, $R^2$, $R^3$, $R^4$, $R^a$ and $R^b$ have the meanings given below.

The remarks made in the following with respect to preferred aspects of the invention, e.g. to preferred meanings of the variables of compound (I), to preferred compounds (I) and to preferred embodiments of the method or the use according to the invention, apply in each case on their own or to combinations thereof.

Preference is given to the compounds of the formula I and to their salts, wherein the moiety R the variables x and y are 0, 1 or 2. Preferably x+y is 1, 2 or 3. In particular x+y is 1 or 2.

Preference is given to the compounds of the formula I and to their salts, wherein the moiety R the variables a and b are 0, 1 or 2. Preferably a+b is 1, 2 or 3. In particular a+b is 1 or 2.

Preferably a+b+x+y is 3, 4, 5 or 6, in particular 3, 4 or 5.

More preference is given to the compounds of the formula I and to their salts, wherein the moiety R the variables a and b are 0, 1 or 2, x and y are 0, 1 or 2, a+b is 1, 2 or 3, x+y is 1, 2 or 3 and a+b+x+y is 3, 4, 5 or 6, in particular 3, 4 or 5.

Preference is given to the compounds of the formula I and to their salts, wherein the moiety R the variable Q is N.

Another embodiment of the invention relates to compounds of the formula I and to their salts, where in the moiety R the variable Q is CH.

Preference is given to the compounds of the formula I and to their salts, wherein the moiety R the variable $R^1$ is hydrogen, $C_1$-$C_4$-alkyl, $C_3$-$C_4$-alkenyl or cyclopropylmethyl. In a particular preferred embodiment, $R^1$ is hydrogen.

Likewise preference is given to the compounds of the formula I and to their salts, wherein the moiety R the variable $R^1$ is benzyl, benzyloxycarbonyl or $C_1$-$C_4$-alkoxycarbonyl such as methoxycarbonyl, ethoxycarbonyl, butoxycarbonyl or tert.-butoxycarbonyl. These compounds are valuable intermediates in the preparation of compounds I, wherein $R^1$ is hydrogen.

Preference is given to the compounds of the formula I and to their salts, wherein the moiety R the variable $R^2$ is hydrogen. Preference is also given to the compounds of the formula I and to their salts, wherein the moiety R the variable $R^3$ is hydrogen. In particular $R^2$ and $R^3$ are both hydrogen.

Preference is given to the compounds of the formula I and to their salts, wherein the moiety R the variable q is 0.

Preference is given to the compounds of the formula I and to their salts, wherein the moiety R the variable p is 0.

Another embodiment of the invention relates to compounds of the formula I and to their salts, where p is 2 and two radicals $R^4$, which are bound to adjacent carbon atoms of X or Y, together are linear $C_2$-$C_5$-alkylene, which is unsubstituted or may carry 1 or 2 radicals $R^6$ as defined herein.

A further embodiment of the invention relates to compounds of the formula I and to their salts, where p is 1 and the radical $R^1$ together with the radical $R^4$, which is bound to a carbon atom of X or Y adjacent to the nitrogen atom, are linear $C_2$-$C_5$-alkylene, which is unsubstituted or may carry 1 or 2 radicals $R^6$ as defined herein.

Particular preference is given to the compounds of the formula I and to their salts, wherein the moiety R the variables a, b, x, y, p, q, Q, $R^1$, $R^2$ and $R^3$ are defined as follows:

a is 0, 1 or 2,
b is 0, 1 or 2,
x is 0, 1 or 2,
y is 0, 1 or 2,
provided that a+b is 1, 2 or 3, x+y is 1, 2 or 3 and a+b+x+y is 3, 4, 5 or 6, in particular 3, 4 or 5,
p is 0,
q is 0,
Q is N,
$R^1$ is hydrogen, $C_1$-$C_4$-alkyl, $C_3$-$C_4$-alkenyl or cyclopropylmethyl, in a particular hydrogen, or $R^1$ is benzyl or butoxycarbonyl,
$R^2$ is hydrogen and
$R^3$ is hydrogen.

Particular preference is given to the compounds of the formula I and to their salts, wherein the moiety R is a radical of the formulae R-1 to R-44:

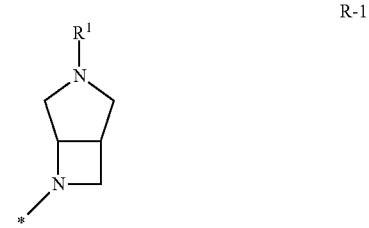

R-1

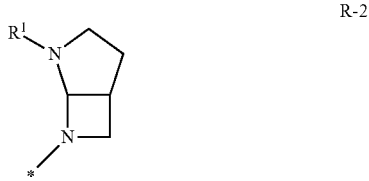

R-2

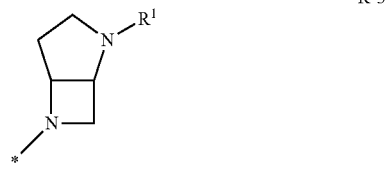

R-3

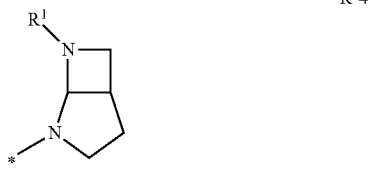

R-4

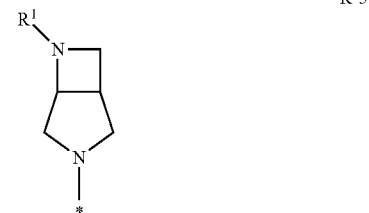

R-5

-continued
R-6
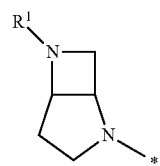
R-7
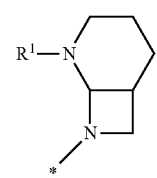
R-8
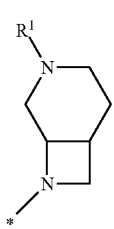
R-9
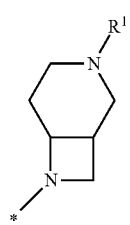
R-10
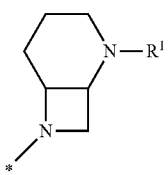
R-11
R-12
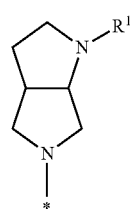
-continued
R-13
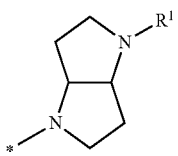
R-14
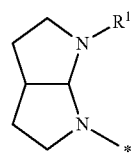
R-15
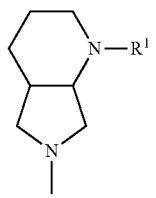
R-16
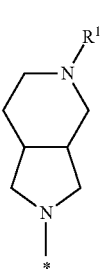
R-17
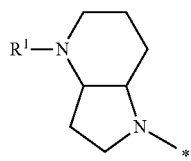
R-18
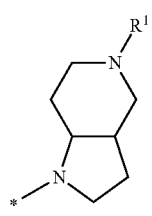
R-19
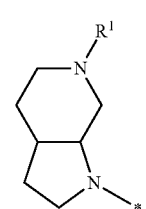
R-20
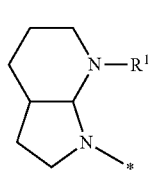

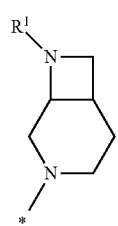
R-21
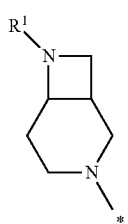
R-22
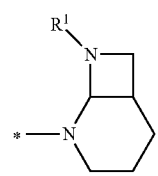
R-23
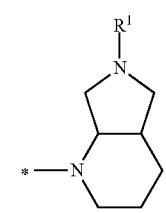
R-24
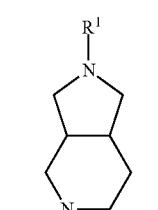
R-25
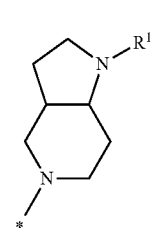
R-26
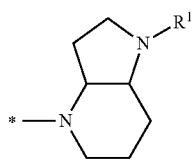
R-28
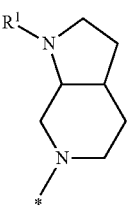
R-29
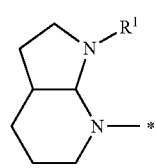
R-30
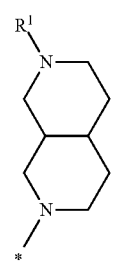
R-31
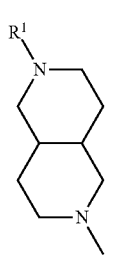
R-32
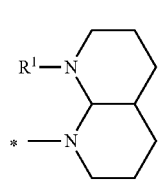
R-33
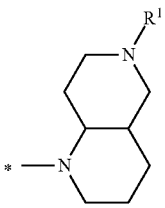
R-34

R-35 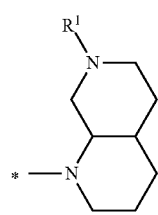

R-36 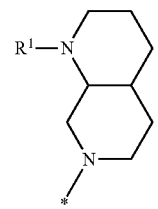

R-37 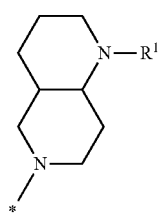

R-38 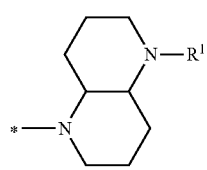

R-39 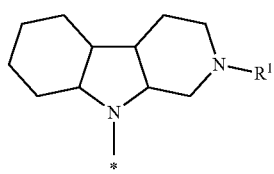

R-40 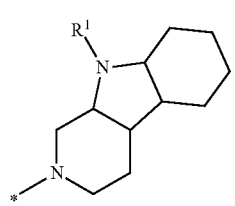

R-41 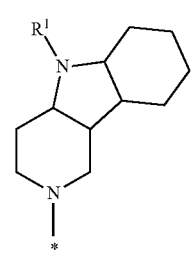

R-42 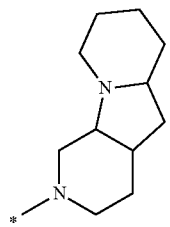

R-43 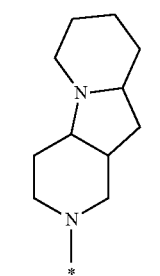

R-44 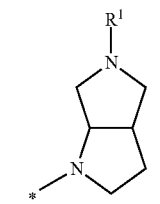

wherein $R^1$ is as defined in claim 1 and * indicates the binding site to the quinolinyl radical.

More preference is given to the compounds of the formula I, their N-oxides and to their salts, wherein the moiety R is selected from the radicals of the formulae R-1 to R-38 and R-44, in particular from the radicals of the formulae R-1, R-3, R-5, R-6, R-8, R-9, R-10, R-11, R-12, R-13, R-15, R-17, R-21, R-22, R-24, R-25, R-27, R-28, R-29, R-34, R-35, R-36, R-37, R-38 and R-44. Particular preference is given to the compounds of the formula I, their N-oxides and to their salts, wherein the moiety R is selected from the radicals of the formulae R-5, R-11, R-12, R-15, R-16, R-25, R-26 and R-44, with most preference given to compounds wherein R is selected from R-11 and R-12. Particular preference is also given to compounds of the present invention, wherein R is R-44.

In the polycylic radicals R, the bridging carbon atom (i.e. the carbon atoms carrying $R^2$ and $R^3$, respectively) may create centers of chirality. The invention relates to compounds, wherein R is a mixture of enantionmers as well as to compounds, wherein R is enantiomerically enriched or enantiomerically pure. The possible enantiomers of the radials R, in particular of the radicals R-5, R-12, R-15, R-16, R-25, R-26 and R-44 are shown hereinafter:

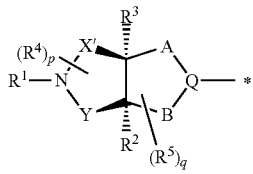

(R-a)

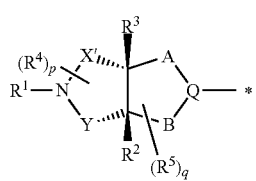
(R-b)
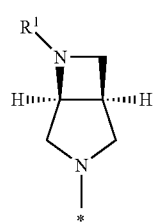
R-5a
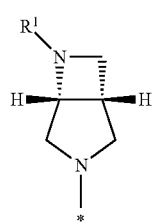
R-5b
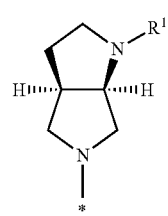
R-12a
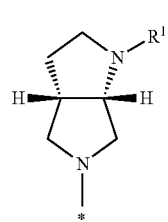
R-12b
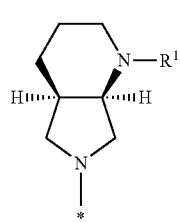
R-15a
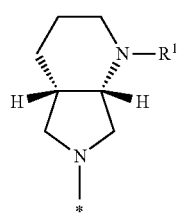
R-15b
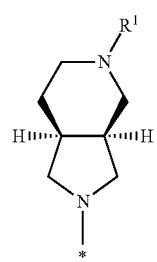
R-16a
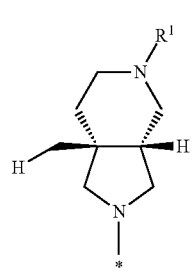
R-16b
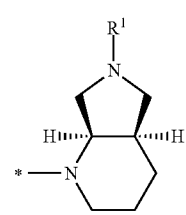
R-25a
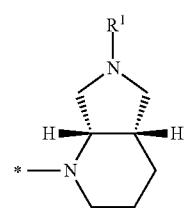
R-25b
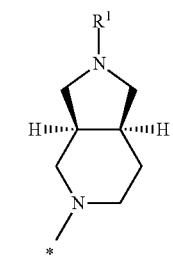
R-26a
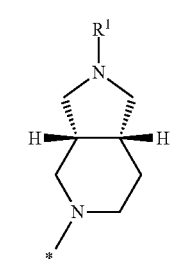
R-26b -continued

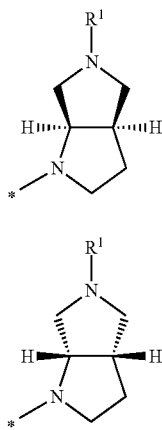

R-44a (top)
R-44b (bottom)

A particular preferred embodiment of the invention relates to compounds of the formula I, wherein X is SO$_2$.

Another embodiment of the invention relates to compounds of the formula I, wherein X is CH$_2$.

A further embodiment of the invention relates to compounds of the formula I, wherein X is a carbonyl group, i.e. X is C(=O).

In one preferred embodiment of the invention X is located in the 3-position of the quinolinyl moiety, i.e. this embodiment relates to compounds of the following formula Ia:

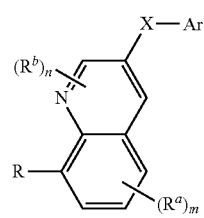

(Ia)

In another embodiment of the invention X is located in the 4-position of the quinolinyl moiety, i.e. this embodiment relates to compounds of the following formula Ib:

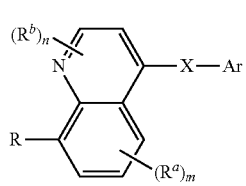

(Ib)

Amongst compounds Ia and Ib, preference is given to those compounds, wherein X is SO$_2$.

Amongst compounds Ia and Ib, preference is given to those compounds Ia, Ib and to their salts, wherein the moiety R the variables a, b, x, y, p, q, Q, R$^1$, R$^2$ and R$^3$ have one of the preferred meanings and in particular are defined as follows:
a is 0, 1 or 2,
b is 0, 1 or 2,
x is 0, 1 or 2,
y is 0, 1 or 2,
provided that a+b is 1, 2 or 3, x+y is 1, 2 or 3 and a+b+x+y is 3, 4, 5 or 6, in particular 3, 4 or 5,
p is 0,
q is 0,
Q is N,
R$^1$ is hydrogen, C$_1$-C$_4$-alkyl, C$_3$-C$_4$-alkenyl or cyclopropylmethyl, in a particular hydrogen, or R$^1$ is benzyl or butoxycarbonyl,
R$^2$ is hydrogen and
R$^3$ is hydrogen.

Amongst compounds Ia and Ib, particular preference is given to those compounds Ia and Ib and to their salts, wherein X is SO$_2$ and wherein R is a moiety of the formulae R-1 to R-44, in particular a moiety R-1, R-3, R-5, R-6, R-8, R-9, R-10, R-11, R-12, R-13, R-15, R-17, R-21, R-22, R-24, R-25, R-27, R-28, R-29, R-34, R-35, R-36, R-37, R-38 or R-44 and more preferably a moiety R-5, R-11, R-12, R-15, R-16, R-25, R-26 or R-44, and most preferably a moiety R-11 or R-12 or R-44, wherein R$^1$ is as defined above and in particular hydrogen.

A very preferred embodiment of the invention relates to compounds of the following formula Ia.a:

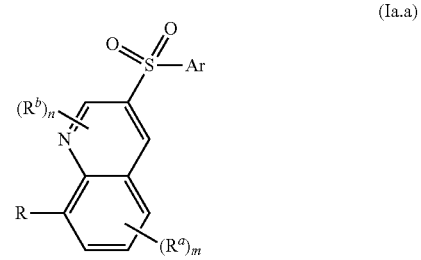

(Ia.a)

wherein n, m, Ar, R$^a$ and R$^b$ are as defined herein and wherein R is as defined above, e.g. a moiety of the formulae R-1 to R-44, in particular a moiety R-1, R-3, R-5, R-6, R-8, R-9, R-10, R-11, R-12, R-13, R-15, R-17, R-21, R-22, R-24, R-25, R-27, R-28, R-29, R-34, R-35, R-36, R-37, R-38 or R-44 and more preferably a moiety R-5, R-11, R-12, R-15, R-16, R-25, R-26 or R-44, and most preferably a moiety R-11 or R-12 or R-44, wherein R$^1$ is as defined above and in particular hydrogen.

Another preferred embodiment of the invention relates to compounds of the following formula Ia.b:

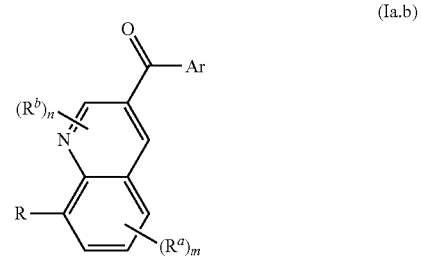

(Ia.b)

wherein n, m, Ar, R$^a$ and R$^b$ are as defined herein and wherein R is as defined above, e.g. a moiety of the formulae R-1 to R-44, in particular a moiety R-1, R-3, R-5, R-6, R-8, R-9, R-10, R-11, R-12, R-13, R-15, R-17, R-21, R-22, R-24, R-25, R-27, R-28, R-29, R-34, R-35, R-36, R-37, R-38 or R-44 and more preferably a moiety R-5, R-11, R-12, R-15, R-16, R-25, R-26 or R-44, and most preferably a moiety R-11 or R-12 or R-44, wherein R$^1$ is as defined above and in particular hydrogen.

A further preferred embodiment of the invention relates to compounds of the following formula Ia.c:

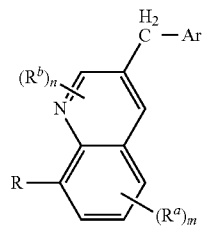

(Ia.c)

wherein n, m, Ar, $R^a$ and $R^b$ are as defined herein and wherein R is as defined above, e.g. a moiety of the formulae R-1 to R-41, in particular a moiety R-1, R-3, R-5, R-6, R-8, R-9, R-10, R-11, R-12, R-13, R-15, R-17, R-21, R-22, R-24, R-25, R-27, R-28, R-29, R-34, R-35, R-36, R-37, R-38 or R-44 and more preferably a moiety R-5, R-11, R-12, R-15, R-16, R-25, R-26 or R-44, and most preferably a moiety R-11 or R-12 or R-44, wherein $R^1$ is as defined above and in particular hydrogen.

A further preferred embodiment of the invention relates to compounds of the following formula Ib.a:

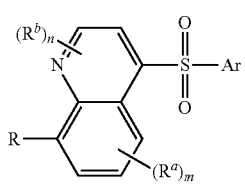

(Ib.a)

wherein n, m, Ar, $R^a$ and $R^b$ are as defined herein and wherein R is as defined above, e.g. a moiety of the formulae R-1 to R-41, in particular a moiety R-1, R-3, R-5, R-6, R-8, R-9, R-10, R-11, R-12, R-13, R-15, R-17, R-21, R-22, R-24, R-25, R-27, R-28, R-29, R-34, R-35, R-36, R-37, R-38 or R-44 and more preferably a moiety R-5, R-11, R-12, R-15, R-16, R-25, R-26 or R-44, and most preferably a moiety R-11 or R-12 or R-44, wherein $R^1$ is as defined above and in particular hydrogen.

Another preferred embodiment of the invention relates to compounds of the following formula Ib.b:

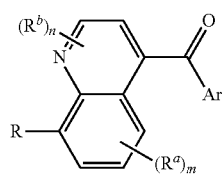

(Ib.b)

wherein n, m, Ar, $R^a$ and $R^b$ are as defined herein and wherein R is as defined above, e.g. a moiety of the formulae R-1 to R-41, in particular a moiety R-1, R-3, R-5, R-6, R-8, R-9, R-10, R-11, R-12, R-13, R-15, R-17, R-21, R-22, R-24, R-25, R-27, R-28, R-29, R-34, R-35, R-36, R-37, R-38 or R-44 and more preferably a moiety R-5, R-11, R-12, R-15, R-16, R-25, R-26 or R-44, and most preferably a moiety R-11 or R-12 or R-44, wherein $R^1$ is as defined above and in particular hydrogen.

A further preferred embodiment of the invention relates to compounds of the following formula Ia.c:

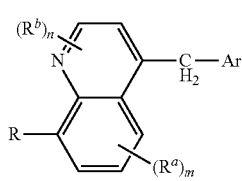

(Ib.c)

wherein n, m, Ar, $R^a$ and $R^b$ are as defined herein and wherein R is as defined above, e.g. a moiety of the formulae R-1 to R-41, in particular a moiety R-1, R-3, R-5, R-6, R-8, R-9, R-10, R-11, R-12, R-13, R-15, R-17, R-21, R-22, R-24, R-25, R-27, R-28, R-29, R-34, R-35, R-36, R-37, R-38 or R-44 and more preferably a moiety R-5, R-11, R-12, R-15, R-16, R-25, R-26 or R-44, and most preferably a moiety R-11 or R-12 or R-44, wherein $R^1$ is as defined above and in particular hydrogen.

A particularly preferred embodiment of the invention relates to compounds of the following formula Ia.a1:

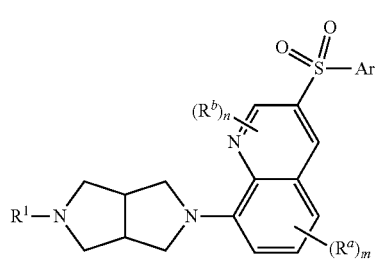

(Ia.a1)

wherein n, m, Ar, $R^1$, $R^a$ and $R^b$ are as defined herein. $R^1$ is in particular hydrogen.

Another particularly preferred embodiment of the invention relates to compounds of the following formula Ia.a2:

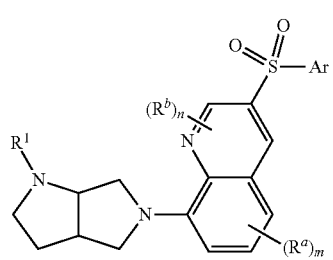

(Ia.a2)

wherein n, m, Ar, $R^1$, $R^a$ and $R^b$ are as defined herein. $R^1$ is in particular hydrogen.

A further particularly preferred embodiment of the invention relates to compounds of the following formula Ia.a2a:

(Ia.a2a)

wherein n, m, Ar, $R^1$, $R^a$ and $R^b$ are as defined herein. $R^1$ is in particular hydrogen.

A further particularly preferred embodiment of the invention relates to compounds of the following formula Ia.a2b:

(Ia.a2b)

wherein n, m, Ar, $R^1$, $R^a$ and $R^b$ are as defined herein. $R^1$ is in particular hydrogen.

A further preferred embodiment of the invention relates to compounds of the formula Ia.a as defined above, wherein R is a radical R-1, wherein $R^1$ is as defined above and wherein $R^1$ is in particular hydrogen (Compounds Ia.a3).

A further preferred embodiment of the invention relates to compounds of the formula Ia.a as defined above, wherein R is a radical R-3, wherein $R^1$ is as defined above and wherein $R^1$ is in particular hydrogen (Compounds Ia.a4).

A further preferred embodiment of the invention relates to compounds of the formula Ia.a as defined above, wherein R is a radical R-5, wherein $R^1$ is as defined above and wherein $R^1$ is in particular hydrogen (Compounds Ia.a5).

A further preferred embodiment of the invention relates to compounds of the formula Ia.a as defined above, wherein R is a radical R-5a, wherein $R^1$ is as defined above and wherein $R^1$ is in particular hydrogen (Compounds Ia.a5a).

A further preferred embodiment of the invention relates to compounds of the formula Ia.a as defined above, wherein R is a radical R-5b, wherein $R^1$ is as defined above and wherein $R^1$ is in particular hydrogen (Compounds Ia.a5b).

A further preferred embodiment of the invention relates to compounds of the formula Ia.a as defined above, wherein R is a radical R-6, wherein $R^1$ is as defined above and wherein $R^1$ is in particular hydrogen (Compounds Ia.a6).

A further preferred embodiment of the invention relates to compounds of the formula Ia.a as defined above, wherein R is a radical R-8, wherein $R^1$ is as defined above and wherein $R^1$ is in particular hydrogen (Compounds Ia.a7).

A further preferred embodiment of the invention relates to compounds of the formula Ia.a as defined above, wherein R is a radical R-9, wherein $R^1$ is as defined above and wherein $R^1$ is in particular hydrogen (Compounds Ia.a8).

A further preferred embodiment of the invention relates to compounds of the formula Ia.a as defined above, wherein R is a radical R-10, wherein $R^1$ is as defined above and wherein $R^1$ is in particular hydrogen (Compounds Ia.a9).

A further preferred embodiment of the invention relates to compounds of the formula Ia.a as defined above, wherein R is a radical R-13, wherein $R^1$ is as defined above and wherein $R^1$ is in particular hydrogen (Compounds Ia.a10).

A further preferred embodiment of the invention relates to compounds of the formula Ia.a as defined above, wherein R is a radical R-15, wherein $R^1$ is as defined above and wherein $R^1$ is in particular hydrogen (Compounds Ia.a11).

A further preferred embodiment of the invention relates to compounds of the formula Ia.a as defined above, wherein R is a radical R-15a, wherein $R^1$ is as defined above and wherein $R^1$ is in particular hydrogen (Compounds Ia.a11a).

A further preferred embodiment of the invention relates to compounds of the formula Ia.a as defined above, wherein R is a radical R-15b, wherein $R^1$ is as defined above and wherein $R^1$ is in particular hydrogen (Compounds Ia.a11b).

A further preferred embodiment of the invention relates to compounds of the formula Ia.a as defined above, wherein R is a radical R-17, wherein $R^1$ is as defined above and wherein $R^1$ is in particular hydrogen (Compounds Ia.a12).

A further preferred embodiment of the invention relates to compounds of the formula Ia.a as defined above, wherein R is a radical R-21, wherein $R^1$ is as defined above and wherein $R^1$ is in particular hydrogen (Compounds Ia.a13).

A further preferred embodiment of the invention relates to compounds of the formula Ia.a as defined above, wherein R is a radical R-22, wherein $R^1$ is as defined above and wherein $R^1$ is in particular hydrogen (Compounds Ia.a14).

A further preferred embodiment of the invention relates to compounds of the formula Ia.a as defined above, wherein R is a radical R-24, wherein $R^1$ is as defined above and wherein $R^1$ is in particular hydrogen (Compounds Ia.a15).

A further preferred embodiment of the invention relates to compounds of the formula Ia.a as defined above, wherein R is a radical R-25, wherein $R^1$ is as defined above and wherein $R^1$ is in particular hydrogen (Compounds Ia.a16).

A further preferred embodiment of the invention relates to compounds of the formula Ia.a as defined above, wherein R is a radical R-25a, wherein $R^1$ is as defined above and wherein $R^1$ is in particular hydrogen (Compounds Ia.a16a).

A further preferred embodiment of the invention relates to compounds of the formula Ia.a as defined above, wherein R is a radical R-25b, wherein $R^1$ is as defined above and wherein $R^1$ is in particular hydrogen (Compounds Ia.a16b).

A further preferred embodiment of the invention relates to compounds of the formula Ia.a as defined above, wherein R is a radical R-27, wherein $R^1$ is as defined above and wherein $R^1$ is in particular hydrogen (Compounds Ia.a17).

A further preferred embodiment of the invention relates to compounds of the formula Ia.a as defined above, wherein R is a radical R-28, wherein $R^1$ is as defined above and wherein $R^1$ is in particular hydrogen (Compounds Ia.a18).

A further preferred embodiment of the invention relates to compounds of the formula Ia.a as defined above, wherein R is a radical R-29, wherein $R^1$ is as defined above and wherein $R^1$ is in particular hydrogen (Compounds Ia.a19).

A further preferred embodiment of the invention relates to compounds of the formula Ia.a as defined above, wherein R is a radical R-34, wherein $R^1$ is as defined above and wherein $R^1$ is in particular hydrogen (Compounds Ia.a20).

A further preferred embodiment of the invention relates to compounds of the formula Ia.a as defined above, wherein R is a radical R-35, wherein $R^1$ is as defined above and wherein $R^1$ is in particular hydrogen (Compounds Ia.a21).

A further preferred embodiment of the invention relates to compounds of the formula Ia.a as defined above, wherein R is a radical R-36, wherein $R^1$ is as defined above and wherein $R^1$ is in particular hydrogen (Compounds Ia.a22).

A further preferred embodiment of the invention relates to compounds of the formula Ia.a as defined above, wherein R is a radical R-37, wherein $R^1$ is as defined above and wherein $R^1$ is in particular hydrogen (Compounds Ia.a23).

A further preferred embodiment of the invention relates to compounds of the formula Ia.a as defined above, wherein R is a radical R-38, wherein $R^1$ is as defined above and wherein $R^1$ is in particular hydrogen (Compounds Ia.a24).

A further preferred embodiment of the invention relates to compounds of the formula Ia.a as defined above, wherein R is a radical R-16, wherein $R^1$ is as defined above and wherein $R^1$ is in particular hydrogen (Compounds Ia.a25).

A further preferred embodiment of the invention relates to compounds of the formula Ia.a as defined above, wherein R is a radical R-16a, wherein $R^1$ is as defined above and wherein $R^1$ is in particular hydrogen (Compounds Ia.a25a).

A further preferred embodiment of the invention relates to compounds of the formula Ia.a as defined above, wherein R is a radical R-16b, wherein $R^1$ is as defined above and wherein $R^1$ is in particular hydrogen (Compounds Ia.a25b).

A further preferred embodiment of the invention relates to compounds of the formula Ia.a as defined above, wherein R is a radical R-26, wherein $R^1$ is as defined above and wherein $R^1$ is in particular hydrogen (Compounds Ia.a26).

A further preferred embodiment of the invention relates to compounds of the formula Ia.a as defined above, wherein R is a radical R-26a, wherein $R^1$ is as defined above and wherein $R^1$ is in particular hydrogen (Compounds Ia.a26a).

A further preferred embodiment of the invention relates to compounds of the formula Ia.a as defined above, wherein R is a radical R-26b, wherein $R^1$ is as defined above and wherein $R^1$ is in particular hydrogen (Compounds Ia.a26b).

A further preferred embodiment of the invention relates to compounds of the formula Ia.a as defined above, wherein R is a radical R-44, wherein $R^1$ is as defined above and wherein $R^1$ is in particular hydrogen (Compounds Ia.a27).

A further preferred embodiment of the invention relates to compounds of the formula Ia.a as defined above, wherein R is a radical R-44a, wherein $R^1$ is as defined above and wherein $R^1$ is in particular hydrogen (Compounds Ia.a27a).

A further preferred embodiment of the invention relates to compounds of the formula Ia.a as defined above, wherein R is a radical R-44b, wherein $R^1$ is as defined above and wherein $R^1$ is in particular hydrogen (Compounds Ia.a27b).

In formula I, and likewise in formulae Ia, Ib, Ia.a, Ia.b, Ia.c, Ia.a1 to Ia.a27, the substituent Ar is preferably a radical $Ar^1$, in particular a radical selected from phenyl, naphthyl, thienyl, pyridyl, pyrimidyl, pyrazolyl, imidazolyl, oxazolyl, isoxazolyl, thiazolyl, triazolyl, thiadiazolyl, quinolinyl, isoquinolinyl, tetrahydroisoquinolinyl, benzofuranyl, benzothiophenyl, benzoxazinyl, benzothiazolyl, benzoxadiazolyl, benzothiadiazolyl, benzomorpholinyl or indanyl, wherein the cyclic radical $Ar^1$ is unsubstituted or may carry 1, 2 or 3 substituents $R^x$ as defined herein. Likewise preferred are compounds of the formula I, wherein Ar is a radical $Ar^2$—$Ar^3$, wherein $Ar^2$ and $Ar^3$ are independently of each other selected from the group consisting of phenyl, thienyl, pyridyl, pyrimidyl, imidazolyl, oxazolyl, isoxazolyl, thiazolyl, triazolyl, thiadiazolyl, wherein the $Ar^1$ and $Ar^2$ are unsubstituted or may carry 1, 2 or 3 substituents $R^x$ as defined herein.

In the radicals $Ar^2$—$Ar^3$, the radical $Ar^2$ is preferably selected from phenyl, pyridyl and thienyl, and the radical $Ar^3$ is preferably phenyl, thienyl, pyridyl, pyrimidyl, pyrazolyl, imidazolyl, oxazolyl, isoxazolyl, thiazolyl, triazolyl or thiadiazolyl, wherein $Ar^1$ and $Ar^2$ are unsubstituted or may carry 1, 2 or 3 substituents $R^x$ as defined herein. Likewise preferred are compounds of the formula I, wherein Ar is a radical $Ar^2$—O—$Ar^3$, wherein $Ar^2$ and $Ar^3$ are independently of each other selected from the group consisting of phenyl, thienyl, pyridyl, pyrimidyl, pyrazolyl, imidazolyl, oxazolyl, isoxazolyl, thiazolyl, triazolyl or thiadiazolyl, wherein $Ar^1$ and $Ar^2$ are unsubstituted or may carry 1, 2 or 3 substituents $R^x$ as defined herein. In the radicals $Ar^2$—$Ar^3$, the radical $Ar^2$ is preferably selected from phenyl, pyridyl and thienyl, and the radical $Ar^3$ is preferably phenyl, wherein $Ar^1$ and $Ar^2$ are unsubstituted or may carry 1, 2 or 3 substituents $R^x$ as defined herein.

In formula I, and likewise in formulae Ia, Ib, Ia.a, Ia.b, Ia.c, Ia.a1 to Ia.a27, the substituent Ar is more preferably phenyl, which is unsubstituted or may carry 1, 2 or 3 substituents $R^x$ as defined herein.

If $R^x$ is present, $R^x$ is preferably selected from halogen, CN, $C_1$-$C_4$-alkyl, $C_1$-$C_4$-haloalkyl, $C_1$-$C_4$-alkoxy, $C_1$-$C_4$-haloalkoxy, $C_3$-$C_6$-cycloalkyl, and a group $NR^{x1}R^{x2}$. More preferably $R^x$ is selected from halogen, $C_1$-$C_4$-haloalkyl, or $C_1$-$C_4$-haloalkoxy.

In formula I, and likewise in formulae Ia, Ib, Ia.a, Ia.b, Ia.c, Ia.a1 to Ia.a27, the variable m is preferably 0. If m is different from 0, $R^a$ is preferably selected from halogen, CN, $C_1$-$C_4$-alkyl, in particular methyl, $OCH_3$, $CF_3$, $CHF_2$, $OCHF_2$ and $OCF_3$.

In formula I, and likewise in formulae Ia, Ib, Ia.a, Ia.b, Ia.c, Ia.a1 to Ia.a27, the variable n is preferably 0. If m is different from 0, $R^b$ is preferably selected from halogen, CN, $C_1$-$C_4$-alkyl, in particular methyl, $OCH_3$, $CF_3$, $CHF_2$, $OCHF_2$ and $OCF_3$.

Examples of preferred compounds of the formula I are given in the following tables 1 to 32b.

Table 1: Compounds of formula I.a.a, wherein m and n are 0 and R is a moiety of the formula R-11, wherein substituents Ar and $R^1$ have the meanings given in one of rows 1 to 225 of table A (compounds Ia.a-1 to Ia.a-225).

TABLE A

| | Ar | $R^1$ |
|---|---|---|
| 1 | phenyl | H |
| 2 | 2-fluorophenyl | H |
| 3 | 3-fluorophenyl | H |
| 4 | 2,3-difluorophenyl | H |
| 5 | 2,4-difluorophenyl | H |
| 6 | 2,5-difluorophenyl | H |
| 7 | 2,6-difluorophenyl | H |
| 8 | 3,4-difluorophenyl | H |
| 9 | 3,5-difluorophenyl | H |
| 10 | 2-chlorophenyl | H |
| 11 | 3-chlorophenyl | H |
| 12 | 2-tolyl | H |
| 13 | 3-tolyl | H |
| 14 | 2-isopropylphenyl | H |
| 15 | 3-isopropylphenyl | H |
| 16 | 2-difluoromethylphenyl | H |
| 17 | 3-difluoromethylphenyl | H |
| 18 | 2-trifluoromethylphenyl | H |
| 19 | 3-trifluoromethylphenyl | H |
| 20 | biphenyl-2-yl | H |
| 21 | biphenyl-3-yl | H |
| 22 | 2-methoxyphenyl | H |
| 23 | 3-methoxyphenyl | H |
| 24 | 2-difluoromethoxyphenyl | H |

TABLE A-continued

| | Ar | R¹ |
|---|---|---|
| 25 | 3-difluoromethoxyphenyl | H |
| 26 | 2-trifluoromethoxyphenyl | H |
| 27 | 3-trifluoromethoxyphenyl | H |
| 28 | 2-phenoxyphenyl | H |
| 29 | 3-phenoxyphenyl | H |
| 30 | 4-(oxazol-5-yl)phenyl | H |
| 31 | 3-(pyrrolidin-1-yl)phenyl | H |
| 32 | 1-naphtyl | H |
| 33 | 2-naphtyl | H |
| 34 | pyridin-2-yl | H |
| 35 | pyridin-3-yl | H |
| 36 | pyridin-4-yl | H |
| 37 | 2-(pyrrolidin-1-yl)pyridin-4-yl | H |
| 38 | 6-morpholinylpyridin-3-yl | H |
| 39 | 6-phenoxypyridin-3-yl | H |
| 40 | thien-2-yl | H |
| 41 | 5-methylthien-2-yl | H |
| 42 | 5-(pyridin-2-yl)thien-2-yl | H |
| 43 | 5-(2-methylthiazol-4-yl)-thien-2-yl | H |
| 44 | 5-chloro-3-methyl-benzo[b]thien-2-yl | H |
| 45 | 2-methylthiazol-5-yl | H |
| 46 | 2,4-dimethyl-thiazol-5-yl | H |
| 47 | 4-methylthiazol-2-yl | H |
| 48 | 5-methylthiazol-2-yl | H |
| 49 | 3,5-dimethylisoxazol-4-yl | H |
| 50 | 1-methylimidazol-4-yl | H |
| 51 | benzothiazol-7-yl | H |
| 52 | 4-methylbenzomorpholin-8-yl | H |
| 53 | quinolin-8-yl | H |
| 54 | isoquinolin-4-yl | H |
| 55 | 2,1,3-benzoxdiazol-4-yl | H |
| 56 | 4-fluorophenyl | H |
| 57 | 4-difluoromethylphenyl | H |
| 58 | 4-trifluoromethylphenyl | H |
| 59 | 4-difluoromethoxyphenyl | H |
| 60 | 4-trifluoromethoxyphenyl | H |
| 61 | 4-methoxyphenyl | H |
| 62 | 4-(oxazol-2-yl)phenyl | H |
| 63 | 4-(oxazol-4-yl)phenyl | H |
| 64 | 3-(oxazol-2-yl)phenyl | H |
| 65 | 3-(oxazol-5-yl)phenyl | H |
| 66 | 3-(oxazol-4-yl)phenyl | H |
| 67 | 3-(piperazin-1-yl)phenyl | H |
| 68 | 3-(morpholin-4-yl)phenyl | H |
| 69 | 3-(4-methylpiperazin-1-yl)phenyl | H |
| 70 | 2-cyanophenyl | H |
| 71 | 3-cyanophenyl | H |
| 72 | 4-cyanophenyl | H |
| 73 | 6-methylpyridin-3-yl | H |
| 74 | 6-trifluormethylpyridin-3-yl | H |
| 75 | 3-(hexahydorpyrrolo[3,4-c]pyrrol-2(1H)-yl)phenyl | H |
| 76 | phenyl | n-propyl |
| 77 | 2-fluorophenyl | n-propyl |
| 78 | 3-fluorophenyl | n-propyl |
| 79 | 2,3-difluorphenyl | n-propyl |
| 80 | 2,4-difluorophenyl | n-propyl |
| 81 | 2,5-difluorophenyl | n-propyl |
| 82 | 2,6-difluorophenyl | n-propyl |
| 83 | 3,4-difluorophenyl | n-propyl |
| 84 | 3,5-difluorophenyl | n-propyl |
| 85 | 2-chlorophenyl | n-propyl |
| 86 | 3-chlorophenyl | n-propyl |
| 87 | 2-tolyl | n-propyl |
| 88 | 3-tolyl | n-propyl |
| 89 | 2-isopropylphenyl | n-propyl |
| 90 | 3-isopropylphenyl | n-propyl |
| 91 | 2-difluoromethylphenyl | n-propyl |
| 92 | 3-difluoromethylphenyl | n-propyl |
| 93 | 2-trifluoromethylphenyl | n-propyl |
| 94 | 3-trifluoromethylphenyl | n-propyl |
| 95 | biphenyl-2-yl | n-propyl |
| 96 | biphenyl-3-yl | n-propyl |
| 97 | 2-methoxyphenyl | n-propyl |
| 98 | 3-methoxyphenyl | n-propyl |
| 99 | 2-difluoromethoxyphenyl | n-propyl |
| 100 | 3-difluoromethoxyphenyl | n-propyl |
| 101 | 2-trifluoromethoxyphenyl | n-propyl |
| 102 | 3-trifluoromethoxyphenyl | n-propyl |
| 103 | 2-phenoxyphenyl | n-propyl |
| 104 | 3-phenoxyphenyl | n-propyl |
| 105 | 4-(oxazol-5-yl)phenyl | n-propyl |
| 106 | 3-(pyrrolidin-1-yl)phenyl | n-propyl |
| 107 | 1-naphtyl | n-propyl |
| 108 | 2-naphtyl | n-propyl |
| 109 | pyridin-2-yl | n-propyl |
| 110 | pyridin-3-yl | n-propyl |
| 111 | pyridin-4-yl | n-propyl |
| 112 | 2-(pyrrolidin-1-yl)pyridin-4-yl | n-propyl |
| 113 | 6-morpholinylpyridin-3-yl | n-propyl |
| 114 | 6-phenoxypyridin-3-yl | n-propyl |
| 115 | thien-2-yl | n-propyl |
| 116 | 5-methylthien-2-yl | n-propyl |
| 117 | 5-(pyridin-2-yl)thien-2-yl | n-propyl |
| 118 | 5-(2-methylthiazol-4-yl)-thien-2-yl | n-propyl |
| 119 | 5-chloro-3-methyl-benzo[b]thien-2-yl | n-propyl |
| 120 | 2-methylthiazol-5-yl | n-propyl |
| 121 | 2,4-dimethyl-thiazol-5-yl | n-propyl |
| 122 | 4-methylthiazol-2-yl | n-propyl |
| 123 | 5-methylthiazol-2-yl | n-propyl |
| 124 | 3,5-dimethylisoxazol-4-yl | n-propyl |
| 125 | 1-methylimidazol-4-yl | n-propyl |
| 126 | benzothiazol-7-yl | n-propyl |
| 127 | 4-methylbenzomorpholin-8-yl | n-propyl |
| 128 | quinolin-8-yl | n-propyl |
| 129 | isoquinolin-4-yl | n-propyl |
| 130 | 2,1,3-benzoxdiazol-4-yl | n-propyl |
| 131 | 4-fluorophenyl | n-propyl |
| 132 | 4-difluoromethylphenyl | n-propyl |
| 133 | 4-trifluoromethylphenyl | n-propyl |
| 134 | 4-difluoromethoxyphenyl | n-propyl |
| 135 | 4-trifluoromethoxyphenyl | n-propyl |
| 136 | 4-methoxyphenyl | n-propyl |
| 137 | 4-(oxazol-2-yl)phenyl | n-propyl |
| 138 | 4-(oxazol-4-yl)phenyl | n-propyl |
| 139 | 3-(oxazol-2-yl)phenyl | n-propyl |
| 140 | 3-(oxazol-5-yl)phenyl | n-propyl |
| 141 | 3-(oxazol-4-yl)phenyl | n-propyl |
| 142 | 3-(piperazin-1-yl)phenyl | n-propyl |
| 143 | 3-(morpholin-4-yl)phenyl | n-propyl |
| 144 | 3-(4-methylpiperazin-1-yl)phenyl | n-propyl |
| 145 | 2-cyanophenyl | n-propyl |
| 146 | 3-cyanophenyl | n-propyl |
| 147 | 4-cyanophenyl | n-propyl |
| 148 | 6-methylpyridin-3-yl | n-propyl |
| 149 | 6-trifluormethylpyridin-3-yl | n-propyl |
| 150 | 3-(hexahydorpyrrolo[3,4-c]pyrrol-2(1H)-yl)phenyl | n-propyl |
| 151 | phenyl | methyl |
| 152 | 2-fluorophenyl | methyl |
| 153 | 3-fluorophenyl | methyl |
| 154 | 2,3-difluorphenyl | methyl |
| 155 | 2,4-difluorophenyl | methyl |
| 156 | 2,5-difluorophenyl | methyl |
| 157 | 2,6-difluorophenyl | methyl |
| 158 | 3,4-difluorophenyl | methyl |
| 159 | 3,5-difluorophenyl | methyl |
| 160 | 2-chlorophenyl | methyl |
| 161 | 3-chlorophenyl | methyl |
| 162 | 2-tolyl | methyl |
| 163 | 3-tolyl | methyl |
| 164 | 2-isopropylphenyl | methyl |
| 165 | 3-isopropylphenyl | methyl |
| 166 | 2-difluoromethylphenyl | methyl |
| 167 | 3-difluoromethylphenyl | methyl |
| 168 | 2-trifluoromethylphenyl | methyl |
| 169 | 3-trifluoromethylphenyl | methyl |
| 170 | biphenyl-2-yl | methyl |
| 171 | biphenyl-3-yl | methyl |
| 172 | 2-methoxyphenyl | methyl |

TABLE A-continued

| | Ar | R¹ |
|---|---|---|
| 173 | 3-methoxyphenyl | methyl |
| 174 | 2-difluoromethoxyphenyl | methyl |
| 175 | 3-difluoromethoxyphenyl | methyl |
| 176 | 2-trifluoromethoxyphenyl | methyl |
| 177 | 3-trifluoromethoxyphenyl | methyl |
| 178 | 2-phenoxyphenyl | methyl |
| 179 | 3-phenoxyphenyl | methyl |
| 180 | 4-(oxazol-5-yl)phenyl | methyl |
| 181 | 3-(pyrrolidin-1-yl)phenyl | methyl |
| 182 | 1-naphtyl | methyl |
| 183 | 2-naphtyl | methyl |
| 184 | pyridin-2-yl | methyl |
| 185 | pyridin-3-yl | methyl |
| 186 | pyridin-4-yl | methyl |
| 187 | 2-(pyrrolidin-1-yl)pyridin-4-yl | methyl |
| 188 | 6-morpholinylpyridin-3-yl | methyl |
| 189 | 6-phenoxypyridin-3-yl | methyl |
| 190 | thien-2-yl | methyl |
| 191 | 5-methylthien-2-yl | methyl |
| 192 | 5-(pyridin-2-yl)thien-2-yl | methyl |
| 193 | 5-(2-methylthiazol-4-yl)-thien-2-yl | methyl |
| 194 | 5-chloro-3-methyl-benzo[b]thien-2-yl | methyl |
| 195 | 2-methylthiazol-5-yl | methyl |
| 196 | 2,4-dimethyl-thiazol-5-yl | methyl |
| 197 | 4-methylthiazol-2-yl | methyl |
| 198 | 5-methylthiazol-2-yl | methyl |
| 199 | 3,5-dimethylisoxazol-4-yl | methyl |
| 200 | 1-methylimidazol-4-yl | methyl |
| 201 | benzothiazol-7-yl | methyl |
| 202 | 4-methylbenzomorpholin-8-yl | methyl |
| 203 | quinolin-8-yl | methyl |
| 204 | isoquinolin-4-yl | methyl |
| 205 | 2,1,3-benzoxdiazol-4-yl | methyl |
| 206 | 4-fluorophenyl | methyl |
| 207 | 4-difluoromethylphenyl | methyl |
| 208 | 4-trifluoromethylphenyl | methyl |
| 209 | 4-difluoromethoxyphenyl | methyl |
| 210 | 4-trifluoromethoxyphenyl | methyl |
| 211 | 4-methoxyphenyl | methyl |
| 212 | 4-(oxazol-2-yl)phenyl | methyl |
| 213 | 4-(oxazol-4-yl)phenyl | methyl |
| 214 | 3-(oxazol-2-yl)phenyl | methyl |
| 215 | 3-(oxazol-5-yl)phenyl | methyl |
| 216 | 3-(oxazol-4-yl)phenyl | methyl |
| 217 | 3-(piperazin-1-yl)phenyl | methyl |
| 218 | 3-(morpholin-4-yl)phenyl | methyl |
| 219 | 3-(4-methylpiperazin-1-yl)phenyl | methyl |
| 220 | 2-cyanophenyl | methyl |
| 221 | 3-cyanophenyl | methyl |
| 222 | 4-cyanophenyl | methyl |
| 223 | 6-methylpyridin-3-yl | methyl |
| 224 | 6-trifluormethylpyridin-3-yl | methyl |
| 225 | 3-(hexahydorpyrrolo[3,4-c]pyrrol-2(1H)-yl)phenyl | methyl |

Table 2: Compounds of formula I.a.a, wherein m and n are 0 and R is a moiety of the formula R-12, wherein the substituents Ar and R¹ have the meanings given in one of rows 1 to 225 of table A (compounds Ia.a-226 to Ia.a-450).

Table 2a: Compounds of formula I.a.a, wherein m and n are 0 and R is a moiety of the formula R-12a, wherein the substituents Ar and R¹ have the meanings given in one of rows 1 to 225 of table A (compounds Ia.a-226a to Ia.a-450a).

Table 2b: Compounds of formula I.a.a, wherein m and n are 0 and R is a moiety of the formula R-12b, wherein the substituents Ar and R¹ have the meanings given in one of rows 1 to 225 of table A (compounds Ia.a-226b to Ia.a-450b).

Table 3: Compounds of formula I.b.a, wherein m and n are 0 and R is a moiety of the formula R-11, wherein the substituents Ar and R¹ have the meanings given in one of rows 1 to 225 of table A (compounds Ib.a-1 to Ib.a-225).

Table 4: Compounds of formula I.b.a, wherein m and n are 0 and R is a moiety of the formula R-12, wherein the substituents Ar and R¹ have the meanings given in one of rows 1 to 225 of table A (compounds Ib.a-226 to Ib.a1-450).

Table 4a: Compounds of formula I.b.a, wherein m and n are 0 and R is a moiety of the formula R-12a, wherein the substituents Ar and R¹ have the meanings given in one of rows 1 to 225 of table A (compounds Ib.a-226a to Ib.a1-450a).

Table 4b: Compounds of formula I.b.a, wherein m and n are 0 and R is a moiety of the formula R-12a, wherein the substituents Ar and R¹ have the meanings given in one of rows 1 to 225 of table A (compounds Ib.a-226b to Ib.a1-450b).

Table 5: Compounds of formula I.a.b, wherein m and n are 0 and R is a moiety of the formula R-11, wherein the substituents Ar and R¹ have the meanings given in one of rows 1 to 225 of table A (compounds Ia.b-1 to Ia.b-225).

Table 6: Compounds of formula I.a.b, wherein m and n are 0 and R is a moiety of the formula R-12, wherein the substituents Ar and R¹ have the meanings given in one of rows 1 to 225 of table A (compounds Ia.b-226 to Ia.b-450).

Table 6a: Compounds of formula I.a.b, wherein m and n are 0 and R is a moiety of the formula R-12a, wherein the substituents Ar and R¹ have the meanings given in one of rows 1 to 225 of table A (compounds Ia.b-226a to Ia.b-450a).

Table 6b: Compounds of formula I.a.b, wherein m and n are 0 and R is a moiety of the formula R-12b, wherein the substituents Ar and R¹ have the meanings given in one of rows 1 to 225 of table A (compounds Ia.b-226b to Ia.b-450b).

Table 7: Compounds of formula I.a.c, wherein m and n are 0 and R is a moiety of the formula R-11, wherein the substituents Ar and R¹ have the meanings given in one of rows 1 to 225 of table A (compounds Ia.c-1 to Ia.c-225).

Table 8: Compounds of formula I.a.c, wherein m and n are 0 and R is a moiety of the formula R-12, wherein the substituents Ar and R¹ have the meanings given in one of rows 1 to 225 of table A (compounds Ia.c-226 to Ia.c-450).

Table 8a: Compounds of formula I.a.c, wherein m and n are 0 and R is a moiety of the formula R-12a, wherein the substituents Ar and R¹ have the meanings given in one of rows 1 to 225 of table A (compounds Ia.c-226a to Ia.c-450a).

Table 8b: Compounds of formula I.a.c, wherein m and n are 0 and R is a moiety of the formula R-12b, wherein the substituents Ar and R¹ have the meanings given in one of rows 1 to 225 of table A (compounds Ia.c-226b to Ia.c-450b).

Table 9: Compounds of formula I.a.a, wherein m and n are 0 and R is a moiety of the formula R-1, wherein the substituents Ar and R¹ have the meanings given in one of rows 1 to 225 of table A (compounds Ia.a-451 to Ia.a-675).

Table 10: Compounds of formula I.a.a, wherein m and n are 0 and R is a moiety of the formula R-3, wherein the substituents Ar and R¹ have the meanings given in one of rows 1 to 225 of table A (compounds Ia.a-676 to Ia.a-900).

Table 11: Compounds of formula I.a.a, wherein m and n are 0 and R is a moiety of the formula R-5, wherein the substituents Ar and R¹ have the meanings given in one of rows 1 to 225 of table A (compounds Ia.a-901 to Ia.a-1125).

Table 11a: Compounds of formula I.a.a, wherein m and n are 0 and R is a moiety of the formula R-5a, wherein the substituents Ar and R¹ have the meanings given in one of rows 1 to 225 of table A (compounds Ia.a-901a to Ia.a-1125a).

Table 11b: Compounds of formula I.a.a, wherein m and n are 0 and R is a moiety of the formula R-5b, wherein the substituents Ar and R¹ have the meanings given in one of rows 1 to 225 of table A (compounds Ia.a-901b to Ia.a-1125b).

Table 12: Compounds of formula I.a.a, wherein m and n are 0 and R is a moiety of the formula R-8, wherein the substituents Ar and $R^1$ have the meanings given in one of rows 1 to 225 of table A (compounds Ia.a-1126 to Ia.a-1350).

Table 13: Compounds of formula I.a.a, wherein m and n are 0 and R is a moiety of the formula R-9, wherein the substituents Ar and $R^1$ have the meanings given in one of rows 1 to 225 of table A (compounds Ia.a-1351 to Ia.a-1575).

Table 14: Compounds of formula I.a.a, wherein m and n are 0 and R is a moiety of the formula R-10, wherein the substituents Ar and $R^1$ have the meanings given in one of rows 1 to 225 of table A (compounds Ia.a-1576 to Ia.a-1800).

Table 15: Compounds of formula I.a.a, wherein m and n are 0 and R is a moiety of the formula R-13, wherein the substituents Ar and $R^1$ have the meanings given in one of rows 1 to 225 of table A (compounds Ia.a-1801 to Ia.a-2025).

Table 16: Compounds of formula I.a.a, wherein m and n are 0 and R is a moiety of the formula R-15, wherein the substituents Ar and $R^1$ have the meanings given in one of rows 1 to 225 of table A (compounds Ia.a-2026 to Ia.a-2250).

Table 16a: Compounds of formula I.a.a, wherein m and n are 0 and R is a moiety of the formula R-15a, wherein the substituents Ar and $R^1$ have the meanings given in one of rows 1 to 225 of table A (compounds Ia.a-2026a to Ia.a-2250a).

Table 16b: Compounds of formula I.a.a, wherein m and n are 0 and R is a moiety of the formula R-15b, wherein the substituents Ar and $R^1$ have the meanings given in one of rows 1 to 225 of table A (compounds Ia.a-2026b to Ia.a-2250b).

Table 17: Compounds of formula I.a.a, wherein m and n are 0 and R is a moiety of the formula R-17, wherein the substituents Ar and $R^1$ have the meanings given in one of rows 1 to 225 of table A (compounds Ia.a-2251 to Ia.a-2475).

Table 18: Compounds of formula I.a.a, wherein m and n are 0 and R is a moiety of the formula R-21, wherein the substituents Ar and $R^1$ have the meanings given in one of rows 1 to 225 of table A (compounds Ia.a-2476 to Ia.a-2700).

Table 19: Compounds of formula I.a.a, wherein m and n are 0 and R is a moiety of the formula R-22, wherein the substituents Ar and $R^1$ have the meanings given in one of rows 1 to 225 of table A (compounds Ia.a-2701 to Ia.a-2925).

Table 20: Compounds of formula I.a.a, wherein m and n are 0 and R is a moiety of the formula R-24, wherein the substituents Ar and $R^1$ have the meanings given in one of rows 1 to 225 of table A (compounds Ia.a-2926 to Ia.a-3150).

Table 21: Compounds of formula I.a.a, wherein m and n are 0 and R is a moiety of the formula R-25, wherein the substituents Ar and $R^1$ have the meanings given in one of rows 1 to 225 of table A (compounds Ia.a-3151 to Ia.a-3375).

Table 21a: Compounds of formula I.a.a, wherein m and n are 0 and R is a moiety of the formula R-25a, wherein the substituents Ar and $R^1$ have the meanings given in one of rows 1 to 225 of table A (compounds Ia.a-3151a to Ia.a-3375a).

Table 21b: Compounds of formula I.a.a, wherein m and n are 0 and R is a moiety of the formula R-25b, wherein the substituents Ar and $R^1$ have the meanings given in one of rows 1 to 225 of table A (compounds Ia.a-3151b to Ia.a-3375b).

Table 22: Compounds of formula I.a.a, wherein m and n are 0 and R is a moiety of the formula R-27, wherein the substituents Ar and $R^1$ have the meanings given in one of rows 1 to 225 of table A (compounds Ia.a-3376 to Ia.a-3600).

Table 23: Compounds of formula I.a.a, wherein m and n are 0 and R is a moiety of the formula R-28, wherein the substituents Ar and $R^1$ have the meanings given in one of rows 1 to 225 of table A (compounds Ia.a-3601 to Ia.a-3825).

Table 24: Compounds of formula I.a.a, wherein m and n are 0 and R is a moiety of the formula R-29, wherein the substituents Ar and $R^1$ have the meanings given in one of rows 1 to 225 of table A (compounds Ia.a-3826 to Ia.a-4050).

Table 25: Compounds of formula I.a.a, wherein m and n are 0 and R is a moiety of the formula R-34, wherein the substituents Ar and $R^1$ have the meanings given in one of rows 1 to 225 of table A (compounds Ia.a-4051 to Ia.a-4275).

Table 26: Compounds of formula I.a.a, wherein m and n are 0 and R is a moiety of the formula R-35, wherein the substituents Ar and $R^1$ have the meanings given in one of rows 1 to 225 of table A (compounds Ia.a-4276 to Ia.a-4500).

Table 27: Compounds of formula I.a.a, wherein m and n are 0 and R is a moiety of the formula R-36, wherein the substituents Ar and $R^1$ have the meanings given in one of rows 1 to 225 of table A (compounds Ia.a-4501 to Ia.a-4725).

Table 28: Compounds of formula I.a.a, wherein m and n are 0 and R is a moiety of the formula R-37, wherein the substituents Ar and $R^1$ have the meanings given in one of rows 1 to 225 of table A (compounds Ia.a-4726 to Ia.a-4950).

Table 29: Compounds of formula I.a.a, wherein m and n are 0 and R is a moiety of the formula R-38, wherein the substituents Ar and $R^1$ have the meanings given in one of rows 1 to 225 of table A (compounds Ia.a-4951 to Ia.a-5175).

Table 30: Compounds of formula I.a.a, wherein m and n are 0 and R is a moiety of the formula R-16, wherein the substituents Ar and $R^1$ have the meanings given in one of rows 1 to 225 of table A (compounds Ia.a-5176 to Ia.a-5400).

Table 30a: Compounds of formula I.a.a, wherein m and n are 0 and R is a moiety of the formula R-16a, wherein the substituents Ar and $R^1$ have the meanings given in one of rows 1 to 225 of table A (compounds Ia.a-5176a to Ia.a-5400a).

Table 30b: Compounds of formula I.a.a, wherein m and n are 0 and R is a moiety of the formula R-16b, wherein the substituents Ar and $R^1$ have the meanings given in one of rows 1 to 225 of table A (compounds Ia.a-5176b to Ia.a-5400b).

Table 31: Compounds of formula I.a.a, wherein m and n are 0 and R is a moiety of the formula R-26, wherein the substituents Ar and $R^1$ have the meanings given in one of rows 1 to 225 of table A (compounds Ia.a-5401 to Ia.a-5625).

Table 31a: Compounds of formula I.a.a, wherein m and n are 0 and R is a moiety of the formula R-26a, wherein the substituents Ar and $R^1$ have the meanings given in one of rows 1 to 225 of table A (compounds Ia.a-5401a to Ia.a-5625a).

Table 31b: Compounds of formula I.a.a, wherein m and n are 0 and R is a moiety of the formula R-26b, wherein the substituents Ar and $R^1$ have the meanings given in one of rows 1 to 225 of table A (compounds Ia.a-5401b to Ia.a-5625b).

Table 32: Compounds of formula I.a.a, wherein m and n are 0 and R is a moiety of the formula R-44, wherein the substituents Ar and $R^1$ have the meanings given in one of rows 1 to 225 of table A (compounds Ia.a-5626 to Ia.a-5850).

Table 32a: Compounds of formula I.a.a, wherein m and n are 0 and R is a moiety of the formula R-44a, wherein the substituents Ar and $R^1$ have the meanings given in one of rows 1 to 225 of table A (compounds Ia.a-5626a to Ia.a-5850a).

Table 32b: Compounds of formula I.a.a, wherein m and n are 0 and R is a moiety of the formula R-44b, wherein the substituents Ar and $R^1$ have the meanings given in one of rows 1 to 225 of table A (compounds Ia.a-5626b to Ia.a-5850b).

The compounds of the formula I according to the present invention can be obtained as outlined in the synthetic routes below.

1. General Synthetic Pathways

Compounds of the formula I, wherein Q is N can be prepared e.g. starting from suitable 8-halo substituted quinoline compounds of the formula II and polycyclic amines III by a base catalyzed coupling as depicted in scheme 1:

Scheme 1:

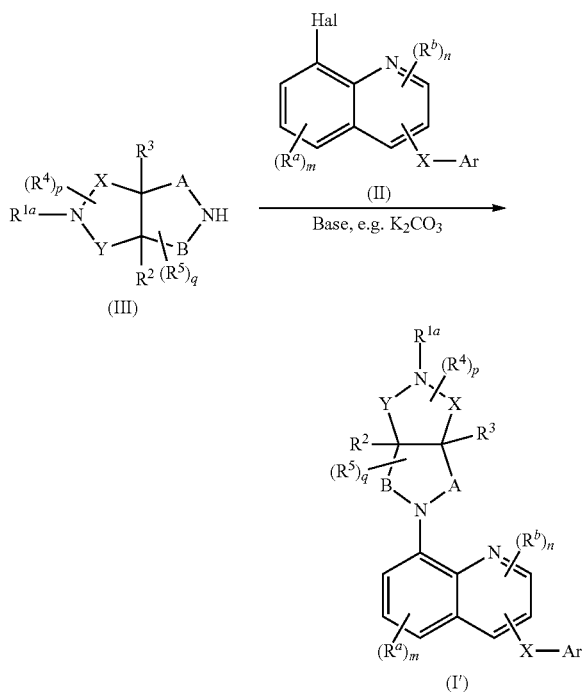

In scheme 1 the variables $R^1$, $R^2$, $R^3$, $R^4$, $R^5$, A, B, X, Y, $R^a$, $R^b$, Ar, m and n are as defined herein. $R^{1a}$ has one of the meanings given for $R^1$, preferably different from hydrogen, or is a suitable N-protecting group, e.g. butyloxycarbonyl (Boc), benzyloxycarbonyl (Cbz), 9-fluorenylmethoxycarbonyl (Fmoc), triphenylmethyl (Trt), nitrobenzenesulfenyl (Nps), allyl or benzyl. Hal is halogen, in particular Br or I.

According to scheme 1 the polycyclic amine compound III is reacted in the presence of a base with a haloquionline compound according to standard processes, e.g. by the processes described in WO 2005/113539 or US 2007/0027161 or without a base in a polar aprotic solvent such as dimethyl sulfoxide (DMSO) as described in Bioorg. Med. Chem. Lett., 2003, 13, 1329. The reaction of the compound II and III can also be performed in the presence of Pd(0)-compound by analogy to the methods described in WO 2002/059107, in particular page 112, WO 03/03197, US 2007/0027161 and Organic Letters, 2003, 5, 897-900.

Suitable bases include alkali metal carbonates, such as lithium carbonate, sodium carbonate, potassium carbonate, alkalimetal hydroxides such as lithium hydroxide, sodium hydroxide and potassium hydroxide, alkalimetal alkoxides such as, sodium methoxide, sodium ethoxide, sodium propoxide, sodium n-butoxide, sodium tert.-butoxide, lithium methoxide, lithium ethoxide, lithium propoxide, lithium n-butoxide, lithium tert.-butoxide, potassium methoxide, potassium ethoxide, potassium propoxide, potassium n-butoxide, potassium tert.-butoxide, alkalimetal hydrides such as lithium hydride, sodium hydride or potassium hydride. The amount of base is preferably at least 0.9 mol per mol of amine III, in particular at least 1.0 mol per mol of amine III, e.g. from 1.1 to 10 mol per mol of amine III.

In a preferred embodiment, the coupling reaction of II and III is performed in the presence of a catalytically effective quantity of a palladium (0) compound or a palladium compound which is capable of forming a palladium(0) compound under reaction conditions, e.g. palladium dichloride, palladium(II) acetate, tetrakis(triphenylphosphine)palladium(0) or tris(dibenzylideneacetone)dipalladium(0) (=Pd2(DBA)$_3$), advantageously in combination with phosphine ligands, e.g. triarylphosphines, such as triphenylphosphine, trialkylphosphines, such as tri-n-butylphosphine, tri-tert.-butylphosphine, and cycloalkylphosphines, such as tricyclohexylphosphine, and especially with phosphine chelate ligands, such as 2,2'-bis(diphenylphosphino)-1,1'-binaphthyl, 1,1'-bis(diphenylphosphino)ferrocene or 1,4-bis(diphenylphosphino)butane. The catalytically effective amount is preferably from 1 to 500 mmol, in particular from 10 to 300 mmol per mol of compound II.

Generally, the coupling reaction of II and III is performed in an inert solvent. Suitable inert solvents include aromatic hydrocarbons such as benzene, toluene, xylenes, ethylbenzene, isopropyl benzene, butylbenzene, tert.-butylbenzene, chlorobenzene, dichlorobenzenes, anisol, aliphatic or alicyclic ethers such as tetrahydrofurane, methyltetrahydrofurane, dioxane, aliphatic or alicyclic sulfones and sulfoxides such as dimethyl sulfoxide, sulfolane and the like, N,N-dialkylamides of aliphatic $C_1$-$C_3$-carboxylic acides and N-alkyllactames such as dimethyl formamide, dimethyl acetamide, N-methylpyrrolidon, N-methylpiperidone, and N-ethylpyrrolidone.

Compounds of the formula I, wherein $R^1$ is hydrogen can be obtained from compounds of the formula I' by cleavage of the N—$R^{12}$-bond, if $R^1$ is a suitable protective group.

If in the resulting quinoline compound I' the radical $R^{12}$ is not the desired radical $R^1$ but a precursor thereof, the compound can be modified as outlined below to obtain the desired substituent $R^1$. A precursor is a radical which can be easily removed and replaced by the desired group $R^1$ or which can be modified to give $R^1$. The precursor can also be an N-protective group (PG), such as butyloxycarbonyl (Boc), benzyloxycarbonyl (Cbz), 9-fluorenylmethoxycarbonyl (Fmoc), triphenylmethyl (Trt), nitrobenzenesulfenyl (Nps), allyl and benzyl.

If $R^{1a}$ is allyl, the allyl group can be cleaved to obtain a compound of the formula I, wherein $R^1$ is hydrogen. The cleavage of the allyl group is achieved, for example, by reacting a compound I' with $R^{1a}$=allyl with an allyl trapping agent, such as mercaptobenzoic acid or 1,3-dimethylbarbituric acid, in the presence of catalytic quantities of palladium (0) compounds or palladium compounds which are able to form a palladium(0) compound under reaction conditions, e.g. palladium dichloride, tetrakis(triphenylphosphine)palladium(0) or tris(dibenzylideneacetone)dipalladium(0), advantageously in combination with phosphine ligands, e.g. triarylphosphines, such as triphenylphosphine, trialkylphosphines, such as tributylphosphine, and cycloalkylphosphines, such as tricyclohexylphosphine, and especially with phosphine chelate ligands, such as 2,2'-bis(diphenylphosphino)-1,1'-binaphthyl or 1,4-bis(diphenylphosphino)butane, applying methods known to a skilled person (with regard to eliminating N-allyl in the presence of mercaptobenzoic acid, see WO 94/24088; with regard to eliminating in the presence of 1,3-dimethylbarbituric acid, see J. Am. Chem. Soc. 2001, 123 (28), pp. 6801-6808 and J. Org. Chem. 2002, 67(11) pp. 3718-3723). Alternatively, the cleavage of N-allyl can also be effected by reacting compound I' with $R^{1a}$ being allyl in the presence of rhodium compounds, such as tris(triphenylphosphine)chlororhodium(I), by analogy to the methods described in J. Chem. Soc., Perkin Transaction I: Organic and Bio-Organic Chemistry 1999 (21) pp. 3089-3104 and Tetrahedron Asymmetry 1997, 8(20), pp. 3387-3391).

If $R^{1a}$ is benzyl, this substituent may also be cleaved to obtain a compound I wherein $R^1$ is H. The reaction conditions for the cleavage are known in the art. Typically, the benzyl group is removed by a hydrogenation reaction in the presence of a suitable Pd catalyst, such as Pd on carbon or palladium hydroxide.

$R^{1a}$ can also be an acid cleavable protective group. The protective group may be removed to yield a compound I, wherein $R^{1a}$ is hydrogen. Suitable protective groups are known in the art and are, for example, selected from tert-butoxycarbonyl (Boc), benzyloxycarbonyl (Cbz), 9-fluorenylmethoxycarbonyl (Fmoc), triphenylmethyl (Trt) and nitrobenzenesulfenyl (Nps). A preferred protective group is Boc. The protective groups can be removed by known methods, such as treatment of the protected amine with an acid, e.g. halogen acid, such as HCl or HBr, formic acid or trifluoroacetic acid, or by hydrogenation, optionally in the presence of a Pd catalyst.

The resulting compound I, wherein $R^1$ is H, can then be reacted, in a known manner, in the sense of an alkylation, with a compound $R^{1b}$—X, wherein $R^{1b}$ has one of the meanings given for $R^1$ which are different from hydrogen. In this compound, $R^{1b}$ is preferably $C_1$-$C_4$-alkyl, $C_3$-$C_6$-cycloalkyl, $C_1$-$C_4$-haloalkyl, $C_1$-$C_4$-alkoxy-$C_1$-$C_4$-alkyl, aryl-$C_1$-$C_4$-alkyl, hetaryl-$C_1$-$C_4$-alkyl or $C_3$-$C_6$-cycloalkyl-$C_1$-$C_4$-alkyl and X is a nucleophilically displaceable leaving group, e.g. halogen, trifluoromethylsulfonate, alkylsulfonate, arylsulfonate, alkyl sulfate and the like. The reaction conditions which are required for the alkylation have been disclosed, e.g. in Bioorganic and Medicinal Chemistry Lett. 2002, 12(7), pp. 2443-2446 and also 2002, 12(5), pp. 1917-1919.

The alkylation can also be achieved, in the sense of a reductive amination, by reacting the compound I, wherein $R^1$=H, with a suitable ketone or aldehyde in the presence of a reducing agent, e.g. in the presence of a borohydride such as sodium borohydride, sodium cyanoborohydride or sodium triacetoxyborohydride. The skilled person is familiar with the reaction conditions which are required for a reductive amination, e.g. from Bioorganic and Medicinal Chemistry Lett. 2002, 12(5), pp. 795-798 and 12(7) pp. 1269-1273.

In case $R^1$ is hydrogen, the compound I can also be reacted with an acyl halide to obtain a compound of the formula I wherein $R^1$ is formyl or $C_1$-$C_3$-alkylcarbonyl. The carbonyl group in these compounds can be reduced with diborane to obtain compounds of the general formula I, wherein $R^1$ is $C_2$-$C_4$-alkyl. The carbonyl group can also be reacted with a fluorinating agent to obtain a compound I wherein $R^1$ is 1,1-difluoroalkyl. Acylation and reduction can be achieved by standard methods, which are discussed in Jerry March, Advanced Organic Chemistry, 3rd ed. J. Wiley & Sons, New York 1985, p. 370 and 373 (acylation) and p. 1099 f. and in the literature cited in this publication (with regard to acylation, see also Synth. Commun. 1986, 16, p. 267, and with regard to reduction, see also J. Heterocycl. Chem. 1979, 16, p. 1525).

Compounds of the formula I, wherein Q is CH can be prepared e.g. starting from suitable 8-halo substituted quinoline compounds of the formula II and polycyclic amines IIIa by a Pd-catalyzed cross-coupling as depicted in scheme 2:

Scheme 2:

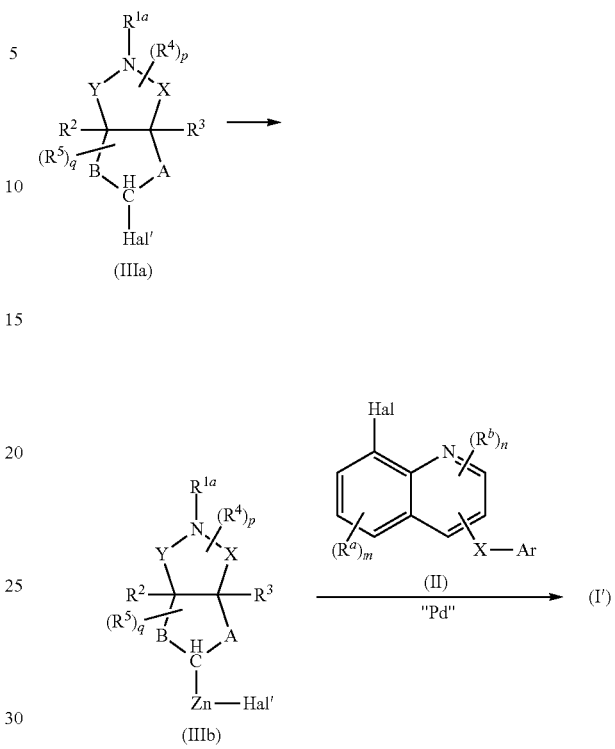

In scheme 2 the variables $R^1$, $R^2$, $R^3$, $R^4$, $R^5$, A, B, X, Y, $R^a$, $R^b$, Ar, m and n are as defined herein. $R^{1a}$ has one of the meanings given for $R^1$, preferably different from hydrogen, or is a suitable N-protecting group, e.g. butyloxycarbonyl (Boc), benzyloxycarbonyl (Cbz), 9-fluorenylmethoxycarbonyl (Fmoc), triphenylmethyl (Trt), nitrobenzenesulfenyl (Nps), allyl or benzyl. Hal and Hal' are halogen, in particular Br or I. According to scheme 2 the halogen compound IIIa is converted into a organozinc compound IIIb according to standard processes, e.g. by the process described in Tetrahedron 1987, 43, 2203-2212; J. Org. Chem. 1988, 53, 2390-2392. The organozinc compound is subsequently reacted in a Negeshi type Pd(0)-mediated cross coupling reaction with an appropriate 8-haloquinoline compound II to give the 8-substituted compound I' by analogy to the method described in Synlett 1998, 4, 379-380; J. Am. Chem. Soc. 2003, 125, 12527-12530. Alternatively, the intermediately generated organozinc compound IIIb can be transmetallized, e.g. with CuCn*2LiCl, and subsequent reacted with a 8-haloquinoline compound of formula II.

The 8-haloquinoline compounds of the formula II are commercially available or they can be prepared according to routine techniques of organic synthesis, which are well known to a person skilled in the art, e.g. by analogy to the method described in WO2003/080580. Compounds of the formula II, wherein X is $S(O)_2$ can be prepared e.g. starting from 8-nitroquinoline compounds of the formula XII as depicted in scheme 3.

Scheme 3:

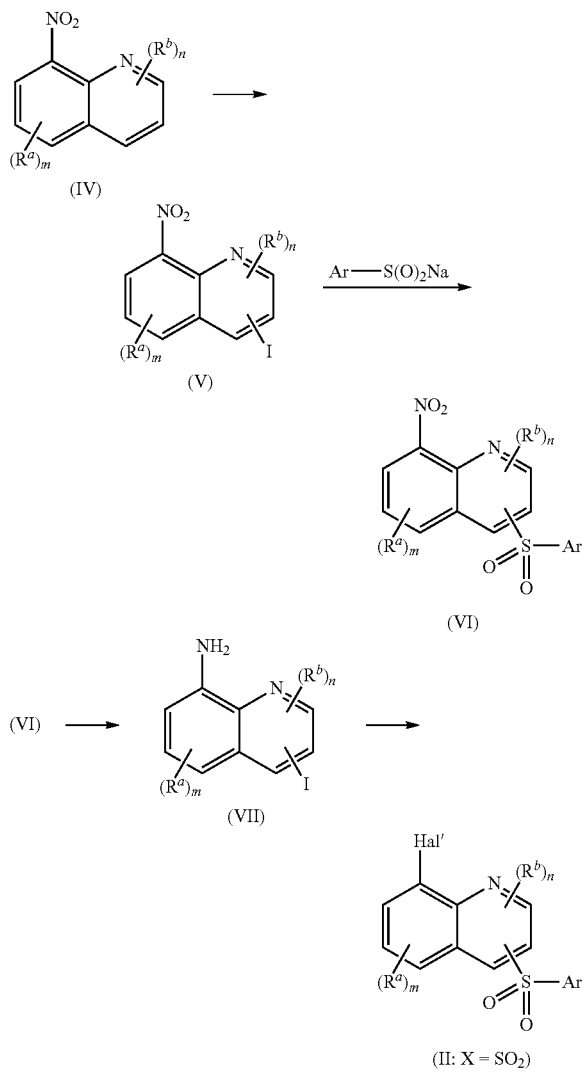

Commercially available nitroquinolines such as IV can be converted to the 3-iodo derivatives V by treatment with an iodinating reagent such as N-iodosuccinimide in a solvent such as acetic acid to yield the 3- or 4-iodoquinoline compound V. The 3- and 4-isomers can be separated at this stage or a later stage. Compound V is then reacted with an alkali metal salt of a sulfinic acid Ar—S(O)OH, e.g. the sodium salt Ar—S(O)$_2$Na, in the presence of a copper (I) salt such as Cu (I) triflate in a polar solvent such as N,N-dimethyl acetamide (DMA) or DMF to yield the quinoline compound VI. Reduction of the nitro group of VI gives the amino compound VII. Reduction can be achieved by a variety methods, including reduction with "non-hydrogen" reducing agent such as SnCl$_2$ or by catalytic hydrogenation techniques familiar to those skilled in the art. The amino group of VII is then converted to the iodo group by a Sandmeyer reaction using a nitrosonium source (e.g. NaNO$_2$, nBuNO$_2$) and a iodide (e.g. CuI or n-Bu$_4$NI) in a suitable solvent such water or CH$_3$CN.

Compounds of the formula III are commercially available or known in the art or can be prepared from the corresponding polycyclic amines having free NH-groups by selective protection/deprotection of the desired NH-groups according to standard techniques of NH-protection as described in P. Kocienski, "Protecting Groups", Thieme Verlag, Stuttgart 2000, pp. 185 to 243 and the references cited therein. Compounds of the formula III have e.g. described in Journal of Medicinal Chemistry (2007), 50(22), 5493-5508, WO 2001/081347, WO 2008/060767, WO 2008/041090, WO 2007/100990, and Bioorganic & Medicinal Chemistry Letters (2006), 16(11), 2891-2894.

If not indicated otherwise, the above-described reactions are generally carried out in a solvent at temperatures between room temperature and the boiling temperature of the solvent employed. Alternatively, the activation energy which is required for the reaction can be introduced into the reaction mixture using microwaves, something which has proved to be of value, in particular, in the case of the reactions catalyzed by transition metals (with regard to reactions using microwaves, see Tetrahedron 2001, 57, p. 9199 ff. p. 9225 ff. and also, in a general manner, "Microwaves in Organic Synthesis", André Loupy (Ed.), Wiley-VCH 2002.

The acid addition salts of compounds I are prepared in a customary manner by mixing the free base with a corresponding acid, where appropriate in solution in an organic solvent, for example acetonitrile, a lower alcohol, such as methanol, ethanol or propanol, an ether, such as diethyl ether, methyl tert-butyl ether or diisopropyl ether, a ketone, such as acetone or methyl ethyl ketone, an ester, such as ethyl acetate, mixtures thereof as well as mixtures thereof with water.

The compound of the invention can be a 5-HT$_6$ receptor agonist, including partial agonistic activity, or a 5-HT$_6$ receptor antagonist, including inverse agonist activity.

The compounds of formula I according to the present invention have a surprisingly high affinity for 5-HT$_6$ receptors. The high affinity of the compounds according to the invention for 5-HT$_6$ receptors is reflected in very low in-vitro receptor binding constants ($K_i$(5-HT$_6$) values) of as a rule less than 50 nM (nmol/l), preferably of less than 10 nM and, in particular of less than 5 nM. The displacement of $^3$H-LSD can, for example, be used in receptor binding studies for determining binding affinities to 5-HT$_6$ receptors.

Furthermore the compounds of formula I are highly selective 5-HT$_6$ receptor ligands which, because of their low affinity for other receptors such as dopamine receptors, adrenergic receptors, muscarinic receptors, histamine receptors, opiate receptors, in particular dopamine D$_2$, $\alpha_1$-adrenergic and histamine H$_1$ receptors, give rise to fewer side-effects than other, less selective 5-HT$_6$ ligands.

For instance the 5-HT$_6$/D$_2$, 5-HT$_6$/$\alpha_1$-adrenergic or 5-HT$_6$/H$_1$ selectivities of the compounds according to the present invention, i.e. the ratios $K_i$(D$_2$)/$K_i$(5-HT$_6$), $K_i$($\alpha_1$-adrenergic)/$K_i$(5-HT$_6$) or $K_i$(H$_1$)/$K_i$(5-HT$_6$) of the receptor binding constants, is as a rule at least 25, preferably at least 50, even better at least 100.

The displacement of [$^3$H]SCH23390 or [$^{125}$I]spiperone can be used, for example, for carrying out receptor binding studies on D$_1$, D$_2$ and D$_4$ receptors.

Furthermore the compounds of formula I because of their structural features are susceptible to display an enhanced brain penetration than other known 5-HT$_6$ receptor ligands.

Because of their binding profile, the compounds can be used for treating diseases which respond to 5-HT$_6$ receptor ligands (or which are susceptible to treatment with a 5-HT$_6$ receptor ligand), i.e. they are effective for treating those medical disorders or diseases in which exerting an influence on (modulating) the 5-HT$_6$ receptors leads to an improvement in the clinical picture or to the disease being cured. Examples of these diseases are disorders or diseases of the central nervous system.

Disorders or diseases of the central nervous system are understood as meaning disorders which affect the spinal cord and, in particular, the brain. Within the meaning of the invention, the term "disorder" denotes disturbances and/or anomalies which are as a rule regarded as being pathological conditions or functions and which can manifest themselves in the form of particular signs, symptoms and/or malfunctions. While the treatment according to the invention can be directed toward individual disorders, i.e. anomalies or pathological conditions, it is also possible for several anomalies, which may be causatively linked to each other, to be combined into patterns, i.e. syndromes, which can be treated in accordance with the invention.

The disorders which can be treated in accordance with the invention are in particular disorders which respond to a modulation of the 5-$HT_6$ receptor. They include cognitive dysfunctions, such as a deficit in memory, cognition and learning, in particular associated with Alzheimer's disease, age-related cognitive decline and mild cognitive impairment, attention deficit disorder/hyperactivity syndrome, personality disorders, such as schizophrenia, in particular cognitive deficits related with schizophrenia, affective disorders such as depression, anxiety and obsessive compulsive disorders, motion or motor disorders such as Parkinson's disease and epilepsy, migraine, sleep disorders (including disturbances of the Circadian rhythm), feeding disorders, such as anorexia and bulimia, certain gastrointestinal disorders such as Irritable Bowl Syndrome, diseases associated with neurodegeneration, such as stroke, spinal or head trauma and head injuries, such as hydrocephalus, drug addiction and obesity.

The addiction diseases include psychic disorders and behavioral disturbances which are caused by the abuse of psychotropic substances, such as pharmaceuticals or narcotics, and also other addiction diseases, such as addiction to gaming (impulse control disorders not elsewhere classified). Examples of addictive substances are: opioids (e.g. morphine, heroin and codeine), cocaine; nicotine; alcohol; substances which interact with the GABA chloride channel complex, sedatives, hypnotics and tranquilizers, for example benzodiazepines; LSD; cannabinoids; psychomotor stimulants, such as 3,4-methylenedioxy-N-methylamphetamine (ecstasy); amphetamine and amphetamine-like substances such as methylphenidate and other stimulants including caffeine. Addictive substances which come particularly into consideration are opioids, cocaine, amphetamine or amphetamine-like substances, nicotine and alcohol.

With regard to the treatment of addiction diseases, particular preference is given to those compounds according to the invention of the formula I which themselves do not possess any psychotropic effect. This can also be observed in a test using rats, which, after having been administered compounds which can be used in accordance with the invention, reduce their self administration of psychotropic substances, for example cocaine.

According to another aspect of the present invention, the compounds according to the invention are suitable for treating disorders whose causes can at least partially be attributed to an anomalous activity of 5-$HT_6$ receptors.

According to another aspect of the present invention, the treatment is directed, in particular, toward those disorders which can be influenced, within the sense of an expedient medicinal treatment, by the binding of preferably exogeneously administered binding partners (ligands) to 5-$HT_6$ receptors.

The diseases which can be treated with the compounds according to the invention are frequently characterized by progressive development, i.e. the above-described conditions change over the course of time; as a rule, the severity increases and conditions may possibly merge into each other or other conditions may appear in addition to those which already exist.

The compounds of formula I can be used to treat a large number of signs, symptoms and/or malfunctions which are connected with the disorders of the central nervous system and, in particular, the abovementioned conditions. These signs, symptoms and/or malfunctions include, for example, a disturbed relationship to reality, lack of insight and ability to meet customary social norms or the demands made by life, changes in temperament, changes in individual drives, such as hunger, sleep, thirst, etc., and in mood, disturbances in the ability to observe and combine, changes in personality, in particular emotional lability, hallucinations, ego-disturbances, distractedness, ambivalence, autism, depersonalization and false perceptions, delusional ideas, chanting speech, lack of synkinesia, short-step gait, flexed posture of trunk and limbs, tremor, poverty of facial expression, monotonous speech, depressions, apathy, impeded spontaneity and decisiveness, impoverished association ability, anxiety, nervous agitation, stammering, social phobia, panic disturbances, withdrawal symptoms in association with dependency, maniform syndromes, states of excitation and confusion, dysphoria, dyskinetic syndromes and tic disorders, e.g. Huntington's chorea and Gilles-de-la-Tourette's syndrome, vertigo syndromes, e.g. peripheral positional, rotational and oscillatory vertigo, melancholia, hysteria, hypochondria and the like.

Within the meaning of the invention, a treatment also includes a preventive treatment (prophylaxis), in particular as relapse prophylaxis or phase prophylaxis, as well as the treatment of acute or chronic signs, symptoms and/or malfunctions. The treatment can be orientated symptomatically, for example as the suppression of symptoms. It can be effected over a short period, be orientated over the medium term or can be a long-term treatment, for example within the context of a maintenance therapy.

The compounds according to the invention are preferentially suitable for treating diseases of the central nervous system, more preferably for treating cognitive dysfunctions and in particular, for treating cognitive dysfunctions associated with schizophrenia or with Alzheimer's disease.

According to another aspect of the invention the compounds of formula (I) are particularly suitable for treating addiction diseases caused for instance by the abuse of psychotropic substances, such as pharmaceuticals, narcotics, nicotine or alcohol, including psychic disorders and behavioral disturbances related thereto.

According to another aspect of the invention the compounds of formula (I) are particularly suitable for treating nutritional disorders, such as obesity, as well as diseases related thereto, such as cardiovascular diseases, digestive diseases, respiratory diseases, cancer or type 2 diabetes.

Within the context of the treatment, the use according to the invention of the described compounds involves a method. In this method, an effective quantity of one or more compounds, as a rule formulated in accordance with pharmaceutical and veterinary practice, is administered to the individual to be treated, preferably a mammal, in particular a human being, productive animal or domestic animal. Whether such a treatment is indicated, and in which form it is to take place, depends on the individual case and is subject to medical assessment (diagnosis) which takes into consideration signs, symptoms and/or malfunctions which are present, the risks of developing particular signs, symptoms and/or malfunctions, and other factors.

As a rule, the treatment is effected by means of single or repeated daily administration, where appropriate together, or alternating, with other active compounds or active compound-containing preparations such that a daily dose of preferably from about 0.1 to 1000 mg/kg of bodyweight, in the case of oral administration, or of from about 0.1 to 100 mg/kg of bodyweight, in the case of parenteral administration, is supplied to an individual to be treated.

The invention also relates to the production of pharmaceutical compositions for treating an individual, preferably a mammal, in particular a human being, productive animal or domestic animal. Thus, the compounds of formula I are customarily administered in the form of pharmaceutical compositions which comprise a pharmaceutically acceptable excipient together with at least one compound according to the invention and, where appropriate, other active compounds. These compositions can, for example, be administered orally, rectally, transdermally, subcutaneously, intravenously, intramuscularly or intranasally.

Examples of suitable pharmaceutical formulations are solid medicinal forms, such as powders, granules, tablets, in particular film tablets, lozenges, sachets, cachets, sugar-coated tablets, capsules, such as hard gelatin capsules and soft gelatin capsules, suppositories or vaginal medicinal forms, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations, and eyedrops and eardrops. Implanted release devices can also be used for administering inhibitors according to the invention. In addition, it is also possible to use liposomes or microspheres.

When producing the compositions, the compounds according to the invention are optionally mixed or diluted with one or more excipients. Excipients can be solid, semisolid or liquid materials which serve as vehicles, carriers or medium for the active compound.

Suitable excipients are listed in the specialist medicinal monographs. In addition, the formulations can comprise pharmaceutically acceptable carriers or customary auxiliary substances, such as glidants; wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik und angrenzende Gebiete [Encyclopedia of auxiliary substances for pharmacy, cosmetics and related fields], 4th edition, Aulendorf: ECV-Editio-Kantor-Verlag, 1996.

The following examples serve to explain the present invention without limiting its scope.

The compounds were either characterized via proton-NMR in d6-dimethylsulfoxid or d-chloroform on a 400 MHz or 500 MHz NMR instrument (Bruker AVANCE), or by mass spectrometry, generally recorded via HPLC-MS in a fast gradient on C18-material (electrospray-ionisation (ESI) mode), or melting point.

The magnetic nuclear resonance spectral properties (NMR) refer to the chemical shifts (δ) expressed in parts per million (ppm). The relative area of the shifts in the $^1$H NMR spectrum corresponds to the number of hydrogen atoms for a particular functional type in the molecule. The nature of the shift, as regards multiplicity, is indicated as singlet (s), broad singlet (s. br.), doublet (d), broad doublet (d br.), triplet (t), broad triplet (t br.), quartet (q), quintet (quint.) and multiplet (m).

8-Nitro-3-(phenylsulfonyl)quinoline was purchased from Insight Chemical Solutions and also prepared using the procedure described in patent application WO2003/80580.

3-Iodo-8-nitroquinoline was purchased from Insight Chemical Solutions and also prepared using the procedure described in patent application WO2003/080580.

Ethyl (3aS,6aS)-hexahydro-pyrrolo[3,4-b]pyrrole-5-carboxylate was prepared using the procedures described in WO 2008060767, WO 2008041090, WO 2007100990, and Bioorganic & Medicinal Chemistry Letters (2006), 16(11), 2891-2894.

Tert.-butyl (3aS,6aS)-hexahydro-pyrrolo[3,4-b]pyrrole-5-carboxylate is commercially available from Focus Synthesis and Enamine.

(1R,5S)-3,6-Diaza-bicyclo[3.2.0]heptane-6-carboxylic acid tert-butyl ester was prepared from (1S,5S)-3,6-Diaza-bicyclo[3.2.0]heptane-3-carboxylic acid phenyl ester via protection of the free amine with di-tert-butyl-dicarbonate and subsequent removal of the benzyloxy-carbonyl group. (1S, 5S)-3,6-Diazabicyclo[3.2.0]heptane-3-carboxylic acid phenyl ester was synthesized according to Journal of Medicinal Chemistry (2007), 50(22), 5493-5508, and WO 2001081347, but is also available commercially from AstaTech.

(1S,5R)-3,6-Diaza-bicyclo[3.2.0]heptane-6-carboxylic acid tert-butyl ester was prepared from (1R,5R)-3,6-Diaza-bicyclo[3.2.0]heptane-3-carboxylic acid phenyl as described for (1R,5S)-3,6-Diaza-bicyclo[3.2.0]heptane-6-carboxylic acid tert-butyl ester.

I. Preparation of the Compounds

Example 1

8-(Hexahydropyrrolo[3,4-b]pyrrol-5(1H)-yl)-3-(phenylsulfonyl)quinoline hydrochloride 1.1 3-(Phenylsulfonyl)quinolin-8-amine To a solution of 8-nitro-3-(phenylsulfonyl)quinoline (3.70 g, 11.77 mmol) in acetic acid (40 ml) at 80° C. was added iron powder (3.29 g, 58.86 mmol) in portions over 5 mins. The resulting suspension was stirred for a further 30 mins. It was then cooled down to room temperature and filtered. The solid was washed with acetic acid and the collected filtrates concentrated. The residue was dissolved in $CH_2Cl_2$ and washed with ammonium hydroxide solution (25%), water and then dried over MgSO4. The organic layer was filtered and then evaporated to afford the title compound (3.20 g, 96%) as a yellow solid.

MS (ESI+) m/z=285.1 $[M+H]^+$ 1.2 8-Iodo-3-(phenylsulfonyl)quinoline

8-Iodo-3-(phenylsulfonyl)quinoline was prepared from 3-(phenylsulfonyl)quinolin-8-amine by the procedure previously described in patent application WO2003080580.

MS (ESI+) m/z=395.9 $[M+H]^+$

1.3 tert-Butyl 5-(3-(phenylsulfonyl)quinolin-8-yl) hexahydropyrrolo[2,3-c]pyrrole-1(2H)-carboxylate A solution of sodium t-butoxide (70 mg, 0.71 mmol) and tert-butyl hexahydropyrrolo-[2,3-c]pyrrole-1(2H)-carboxylate (537 mg, 2.53 mmol) in dioxane (3 mL) was stirred under nitrogen. To this was added 1,1'-bis(diphenylphosphino)ferrocene (25 mg, 0.05 mmol), Pd2(DBA)$_3$ (12 mg, 0.02 mmol) and 8-iodo-3-(phenylsulfonyl)quinoline (200 mg, 0.51 mmol), followed by the addition of a further 2 mL of dioxane. The mixture was then heated at 40° C. for 12 h before partitioning between CH$_2$Cl$_2$ and water. The mixture was filtered through Celite and the organic phase was separated. The water phase was extracted twice with CH$_2$Cl$_2$ and the combined extracts dried (Na$_2$SO$_4$), filtered and concentrated in vacuo to provide the crude material, which was purified by flash chromatography to give the title compound (92 mg, 38%) as a light yellow oil.

MS (ESI+) m/z=480.1 (M+H)$^+$ $^1$H NMR (400 MHz, DMSO): δ (ppm) rotomers 1.38 (d, 9H), 1.82 (m, 1H), 2.02 (m, 1H), 3.00 (m, 1H), 3.40 (m, 2H), 3.68 (m, 2H), 3.82 (m, 1H), 3.95 (m, 1H), 4.25 (m, 1H), 7.02 (s, 1H), 7.53 (s, 2H), 7.65 (m, 5H), 8.09 (d, 1H), 8.97 (s, 1H), 9.10 (br s, 1H).

1.4 8-(Hexahydropyrrolo[3,4-b]pyrrol-5(1H)-yl)-3-(phenylsulfonyl)quinoline hydrochloride A solution of tert-butyl 5-(3-(phenylsulfonyl)quinolin-8-yl)hexahydropyrrolo[2,3-c]pyrrole-1(2H)-carboxylate (92 mg, 0.19 mmol) in CH$_2$Cl$_2$ (5 ml) was treated with hydrochloric acid (4M in dioxane, 2 ml) at 0° C. and then stirred at 50° C. for 16 h. After concentration, the product was washed with EtOAc and dried in vacuo to give the title compound (80 mg, 100% as a white solid.

MS (ESI+) m/z=380.1 (M+H)$^+$ $^1$H NMR (400 MHz, DMSO): δ (ppm) 1.95 (m, 1H), 2.20 (m, 1H), 3.12 (m, 1H), 3.26 (m, 2H), 3.67 (m, 2H), 3.97 (m, 1H), 4.15 (m, 1H), 4.31 (m, 1H), 7.12 (d, 1H), 7.65 (m, 5H), 8.10 (d, 1H), 8.85 (br s, 1H), 9.05 (s, 1H), 9.22 (br s, 1H).

Example 2

Benzyl 6-(3-(phenylsulfonyl)quinolin-8-yl)-3,6-diazabicyclo[3.2.0]heptane-3-carboxylate A solution of sodium t-butoxide (49 mg, 0.51 mmol) and (1S,5S)-benzyl 3,6-diazabicyclo[3.2.0]heptane-3-carboxylate (98 mg, 0.24 mmol) in toluene (3 mL) was stirred under nitrogen. To this was added tri-t-butylphosphine (25 mg, 0.05 mmol), palladium (II) acetate (6.9 mg, 0.03 mmol) and 8-iodo-3-(phenylsulfonyl)quinoline (80 mg, 0.202 mmol). The mixture was then heated at 60° C. for 2 h before partitioning between CH$_2$Cl$_2$ and water. The mixture was filtered through Celite and the organic phase was separated. The water phase was extracted twice with CH$_2$Cl$_2$ and the combined extracts dried (Na$_2$SO$_4$), filtered and concentrated in vacuo to provide the crude material, which was purified by flash chromatography to give the title compound.

MS (ESI+) m/z=500.2 (M+H)$^+$

Example 3 tert-butyl 2-(3-(phenylsulfonyl)quinolin-8-yl) hexahydro-1H-pyrrolo[3,4-c]pyridine-5(6H)-carboxylate A solution of sodium t-butoxide (49 mg, 0.51 mmol) and (1S,5S)-benzyl 3,6-diazabicyclo[3.2.0]heptane-3-carboxylate (98 mg, 0.24 mmol) in toluene (3 mL) was stirred under nitrogen. To this solution tri-t-butylphosphine (25 mg, 0.05 mmol), palladium (II) acetate (6.9 mg, 0.03 mmol) and 8-iodo-3-(phenylsulfonyl)quinoline (80 mg, 0.202 mmol) were added. The mixture was then heated at 60° C. for 2 h. The obtained reaction mixture was then partitioned between CH$_2$Cl$_2$ and water. The mixture was filtered through Celite and the organic phase was separated. The water phase was extracted twice with CH$_2$Cl$_2$ and the combined organic extracts were dried (Na$_2$SO$_4$), filtered and concentrated in vacuo to provide the crude material, which was purified by flash chromatography to give the title compound.

MS (ESI+) m/z=494.5 (M+H)$^+$

Example 4

3-(Phenylsulfonyl)-8-(1H-pyrrolo[3,4-c]pyridin-2 (3H,3aH,4H,5H,6H,-7H,7aH)-yl)quinoline The title compound was prepared by analogy to the procedure of Example 1.4, except using tert-butyl 2-(3-(phenylsulfonyl)quinolin-8-yl)hexahydro-1H-pyrrolo[3,4-c]pyridine-5 (6H)-carboxylate. 25 mg (51%) of the title compound were obtained as a pale yellow solid MS (ESI+) m/z=394.1 (M+H)$^+$

Example 5

(1R,5S)-tert-butyl 3-(3-(phenylsulfonyl)quinolin-8-yl)-3,6-diazabicyclo[3.2.0]heptane-6-carboxylate The title compound was prepared by analogy to the procedure of Example 1.3, except using (1R,5S)-tert-butyl 3,6-diazabicyclo[3.2.0]heptane-6-carboxylate.

MS (ESI+) m/z=465.1 (M+H)$^+$

Example 6

8-((1S,5S)-3,6-diazabicyclo[3.2.0]heptan-3-yl)-3-(phenylsulfonyl)quinoline

The title compound was prepared by analogy to the procedure of Example 1.4, except using (1R,5S)-tert-butyl 3-(3-(phenylsulfonyl)quinolin-8-yl)-3,6-diazabicyclo[3.2.0]heptane-6-carboxylate.

MS (ESI+) m/z=365.1 (M+H)$^+$

Example 7

(3aS,6aS)-ethyl 1-(3-(phenylsulfonyl)quinolin-8-yl) hexahydropyrrolo[3,4-b]pyrrole-5(1H)-carboxylate A solution of 8-fluoro-3-(phenylsulfonyl)quinoline (100 mg, 0.348 mmol), (3aS,6aS)-ethyl hexahydropyrrolo[3,4-b] pyrrole-5(1H)-carboxylate (2R,3R)-2,3-bis(benzoyloxy) succinate (944 mg, 1.74 mmol) and K$_2$CO$_3$ (577 mg) in DMF (3 mL) was stirred under nitrogen and heated at 100° C. for 7 h. The cooled mixture was diluted with 10 mL of saturated NaCl and the resultant precipitate collected and dried to give the title compound.

MS (ESI+) m/z=454.1 (M+H)$^+$

Example 8 tert-butyl 5-(3-(4-fluorophenylsulfonyl)quinolin-8-yl)hexahydropyrrolo[3,4-b]pyrrole-1(2H)-carboxylate The title compound was prepared by analogy to the procedure of Example 1.3, except using 3-(4-fluorophenylsulfonyl)-8-iodoquinoline and tert-butyl hexahydropyrrolo[3,4-b]pyrrole-1(2H)-carboxylate. 250 mg (69%) of the title compound were obtained as a pale yellow oil.
MS (ESI+) m/z=498.2 (M+H)+

Example 9 tert-butyl 5-(3-(phenylsulfonyl)quinolin-8-yl)octahydro-1,5-naphthyridine-1(2H)-carboxylate The title compound was prepared by analogy to the procedure of Example 1.3, except using tert-butyl octahydro-1,5-naphthyridine-1(2H)-carboxylate. 120 mg (9%) of the title compound were obtained as a pale yellow oil.
MS (ESI+) m/z=508.2 (M+H)+

Example 10

1-(3-(phenylsulfonyl)quinolin-8-yl)decahydro-1,5-naphthyridine

The title compound was prepared by analogy to the procedure of Example 1.4, except using tert-butyl 5-(3-(phenylsulfonyl)quinolin-8-yl)octahydro-1,5-naphthyridine-1(2H)-carboxylate. 1 mg (8%) of the title compound were obtained as a pale yellow oil.
MS (ESI+) m/z=408.2 (M+H)+

Example 11 tert-butyl 2-(3-(4-fluorophenylsulfonyl)quinolin-8-yl)hexahydro-1H-pyrrolo[3,4-c]pyridine-5(6H)-carboxylate The title compound was prepared by analogy to the procedure of Example 1.3, except using tert-butyl hexahydro-1H-pyrrolo[3,4-c]pyridine-5(6H)-carboxylate and 3-(4-fluorophenylsulfonyl)-8-iodoquinoline. 130 mg (55%) of the title compound were obtained as a pale yellow oil.
MS (ESI+) m/z=512.2 (M+H)+

Example 12

8-((3aS,6aS)-hexahydropyrrolo[3,4-b]pyrrol-1(2H)-yl)-3-(phenylsulfonyl)-quinoline A solution of (3aS,6aS)-ethyl 1-(3-(phenylsulfonyl)quinolin-8-yl)hexahydropyrrolo[3,4-b]pyrrole-5(1H)-carboxylate (60 mg, 0.133 mmol) and trimethylsilyl-iodide (160 mg, 0.797 mmol) in chloroform (1 mL) was stirred at reflux for 1.5 h. Methanol (4 mg) was added and the solution was partitioned between ethyl acetate and aqueous NaOH (1M). The organic extract was dried (MgSO$_4$), filtered and concentrated to yield 11 mg (22%) of the title compound as a pale yellow oil.
MS (ESI+) m/z=380.1 (M+H)+

Example 13

3-(4-fluorophenylsulfonyl)-8-(1H-pyrrolo[3,4-c]pyridin-2(3H,3aH,4H,5H,6H,7H,7aH)-yl)quinoline The title compound was prepared by analogy to the procedure of Example 1.4, except using tert-butyl 2-(3-(4-fluorophenylsulfonyl)quinolin-8-yl)hexahydro-1H-pyrrolo[3,4-c]pyridine-5(6H)-carboxylate. 81 mg (77%) of the title compound were obtained as a pale yellow oil.
MS (ESI+) m/z=412.2 (M+H)+

Example 14

3-(4-fluorophenylsulfonyl)-8-(hexahydropyrrolo[3,4-c]pyrrol-2(1H)-yl)quinoline

The title compound was prepared by analogy to the procedure of Example 1.4, except using tert-butyl 5-(3-(4-fluorophenylsulfonyl)quinolin-8-yl)hexahydropyrrolo[3,4-c]pyrrole-2(1H)-carboxylate. 121 mg (92%) of the title compound were obtained as a pale yellow oil.
MS (ESI+) m/z=398.1 (M+H)+

Example 15 tert-butyl 5-(3-(3-(trifluoromethoxy)phenylsulfonyl)quinolin-8-yl)hexahydropyrrolo[3,4-c]pyrrole-2(1H)-carboxylate The title compound was prepared by analogy to the procedure of Example 1.3, except using tert-butyl hexahydropyrrolo[3,4-c]pyrrole-2(1H)-carboxylate and 8-iodo-3-(3-(trifluoromethoxy)phenylsulfonyl)quinoline. 140 mg (79%) of the title compound were obtained as a pale yellow solid.
MS (ESI+) m/z=564.2 (M+H)+

Example 16

8-(hexahydropyrrolo[3,4-c]pyrrol-2(1H)-yl)-3-(3-(trifluoromethoxy)-phenylsulfonyl)quinoline The title compound was prepared by analogy to the procedure of Example 1.4, except using tert-butyl 5-(3-(3-(trifluoromethoxy)phenylsulfonyl)quinolin-8-yl)hexahydro-pyrrolo[3,4-c]pyrrole-2(1H)-carboxylate. 79 mg (74%) of the title compound were obtained as a pale yellow oil.
MS (ESI+) m/z=464.1 (M+H)+

Example 17 tert-butyl 5-(3-(3-(5-(tert-butoxycarbonyl)hexahydropyrrolo[3,4-c]pyrrol-2(1H)-yl)phenylsulfonyl)quinolin-8-yl)hexahydropyrrolo[3,4-c]pyrrole-2(1H)-carboxylate The title compound was prepared by analogy to the procedure of 1.3, except using tert-butyl hexahydropyrrolo[3,4-c]pyrrole-2(1H)-carboxylate and 3-(3-bromophenylsulfonyl)-8-iodoquinoline. 18 mg (12%) of the title compound were obtained as a pale yellow solid
MS (ESI+) m/z=690.3 (M+H)+

Example 18

8-(hexahydropyrrolo[3,4-c]pyrrol-2(1H)-yl)-3-(3-(hexahydropyrrolo[3,4-c]pyrrol-2(1H)-yl)phenylsulfonyl)quinoline The title compound was prepared by analogy to the procedure of Example 1.4, except using tert-butyl 5-(3-(3-(5-(tert-butoxycarbonyl)hexahydropyrrolo[3,4-c]pyrrol-2(1H)-yl)phenylsulfonyl)quinolin-8-yl)hexahydropyrrolo[3,4-c]pyrrole-2(1H)-carboxylate. 9 mg (58%) of the title compound were obtained as a pale yellow oil.
MS (ESI+) m/z=490.1 (M+H)+

Example 19 tert-butyl 2-(3-(3-(trifluoromethoxy)phenylsulfonyl)quinolin-8-yl)hexahydro-1H-pyrrolo[3,4-c]pyridine-5(6H)-carboxylate The title compound was prepared by analogy to the procedure of Example 1.3, except using tert-butyl hexahydro-1H-pyrrolo[3,4-c]pyridine-5(6H)-carboxylate and 8-iodo-3-(3-(trifluoromethoxy)phenylsulfonyl)quinoline. 130 mg (54%) of the title compound were obtained as a pale yellow solid.
MS (ESI+) m/z=578.2 (M+H)$^+$

Example 20

8-(1H-pyrrolo[3,4-c]pyridin-2(3H,3aH,4H,5H,6H,7H,7aH)-yl)-3-(3-(trifluoromethoxy)phenylsulfonyl)quinoline The title compound was prepared by analogy to the procedure of Example 1.4, except using tert-butyl 2-(3-(3-(trifluoromethoxy)phenylsulfonyl)quinolin-8-yl)hexahydro-1H-pyrrolo[3,4-c]pyridine-5(6H)-carboxylate. 67 mg (63%) of the title compound were obtained as a pale yellow oil.
MS (ESI+) m/z=478.1 (M+H)$^+$

Example 21 tert-butyl 5-(3-(3-(trifluoromethyl)phenylsulfonyl)quinolin-8-yl)hexahydropyrrolo[3,4-b]pyrrole-1(2H)-carboxylate The title compound was prepared by analogy to the procedure of Example 1.3, except using tert-butyl hexahydropyrrolo[3,4-b]pyrrole-1(2H)-carboxylate and 8-iodo-3-(3-(trifluoromethyl)phenylsulfonyl)quinoline. 133 mg (56%) of the title compound were obtained as a pale yellow solid.
MS (ESI+) m/z=548.2 (M+H)$^+$

Example 22

8-(hexahydropyrrolo[3,4-b]pyrrol-5(1H)-yl)-3-(3-(trifluoromethyl)-phenylsulfonyl)quinoline The title compound was prepared by analogy to the procedure of Example 1.4, except using tert-butyl 5-(3-(3-(trifluoromethyl)phenylsulfonyl)quinolin-8-yl)hexahydro-pyrrolo[3,4-b]pyrrole-1(2H)-carboxylate. 17 mg (17%) of the title compound were obtained as a pale yellow oil.
MS (ESI+) m/z=448.1 (M+H)$^+$

Example 23

(3aR,6aS)-tert-butyl 5-(3-(3-(trifluoromethyl)phenylsulfonyl)quinolin-8-yl)hexahydropyrrolo[3,4-c]pyrrole-2(1H)-carboxylate The title compound was prepared by analogy to the procedure of Example 1.3, except using (3aR,6aS)-tert-butyl hexahydropyrrolo[3,4-c]pyrrole-2(1H)-carboxylate and 8-iodo-3-(3-(trifluoromethyl)phenylsulfonyl)quinoline. 107 mg (60%) of the title compound were obtained as a pale yellow solid.
MS (ESI+) m/z=548.2 (M+H)$^+$

Example 24

8-((3aR,6aS)-hexahydropyrrolo[3,4-c]pyrrol-2(1H)-yl)-3-(3-(trifluoromethyl)phenylsulfonyl)quinoline The title compound was prepared by analogy to the procedure of Example 1.4, except using (3aR,6aS)-tert-butyl 5-(3-(3-(trifluoromethyl)phenylsulfonyl)quinolin-8-yl)hexahydropyrrolo[3,4-c]pyrrole-2(1H)-carboxylate. 103 mg (97%) of the title compound were obtained as a pale yellow oil.
MS (ESI+) m/z=448.1 (M+H)$^+$

Example 25

(3aS,6aS)-ethyl-1-(3-(3-fluorophenylsulfonyl)quinolin-8-yl)hexahydro-pyrrolo[3,4-b]pyrrole-5(1H)-carboxylate

25.1 3-(3-fluorophenylsulfonyl)-8-nitroquinoline 15 g of 3-iodo-8-nitroquinoline (50 mmol), 0.476 g CuJ (2.5 mmol) and 21.22 g K$_3$PO$_4$ (100 mmol) were suspended in 150 ml of ethylene glycol. 9.61 g 3-fluorobenzenethiol were added and the reaction mixture was stirred at 80° C. for 6 h followed by stirring for 14 h at room temperature. The reaction mixture was partitioned between 150 ml of dichloromethane and 150 ml of water, and after stirring for 15 min, the organic phase was separated. The aqueous layer was extracted one more time with dichloromethane, the combined organic layers were washed with water and stirred with 5 g charcoal for 15 min. The filtrate was added to a suspension of 54.1 g (87 mmol) monoperoxy-phthalic acid magnesium salt hexahydrate in 300 ml of dichloromethane/methanol at 10-25° C. within 30 min. After stirring for 16 h at room temperature, the reaction mixture was cooled and slowly 250 mL of an aqueous sodium pyrosulfite solution were added. The organic phase and the precipitate were separated and washed with 250 ml of aqueous sodium bicarbonate solution. After stirring for 15 min, the precipitate was filtered, washed with water and ether, and dried under vacuum to yield 11.7 g of the product.
MS (ESI+) m/z=333.0 [M+H]$^+$

25.2 3-(3-fluorophenylsulfonyl)quinolin-8-amine 10.13 g of 3-(3-fluorophenylsulfonyl)-8-nitroquinoline (30.5 mmol) were suspended in 150 ml of acetic acid and warmed to 110° C. 8.51 g of iron powder (152 mmol) were added in small portions with stirring. Stirring was continued for 1 h. Then, the reaction mixture was cooled to room temperature, partitioned between water and ethyl acetate. The organic phase was separated and the aqueous layer was extracted three times with ethyl acetate. Water was added to the combined organic layers and the pH was adjusted to alkaline conditions with aqueous ammonia solution under rapid stirring. The organic layer was separated, extracted twice with water, dried over magnesium sulfate, filtered and the solvents were evaporated to yield 9.2 g of the product.
MS (ESI+) m/z=303.0 [M+H]$^+$

25.3 3-(3-fluorophenylsulfonyl)-8-iodo-quinoline 9.214 g of 3-(3-fluorophenylsulfonyl)quinolin-8-amine (30.5 mmol) were dissolved in 50 ml of trifluoroacetic acid.

The mixture was concentrated to yield the trifluoroacetate salt, which was then dissolved in acetonitrile. 4.71 g of n-butylnitrite (45.7 mmol) in 150 ml of acetonitrile were cooled to 0° C. and the acetonitrile solution of the trifluoroacetate salt of 3-(3-fluorophenylsulfonyl)quinolin-8-amine (dissolved in 100 mL acetonitrile) was added dropwise at 0-+5° C. After stirring for 10 min, 22.52 g of tetra-n-butylammonium iodide were added in portions and the reaction mixture was stirred for 2 h at ~0° C. After evaporation of the solvents, the residue was dissolved in dichloromethane and washed twice with a 10% aqueous sodium thiosulfate solution. The organic phase was evaporated to dryness and the residue was treated with isoproanol. The precipitate was filtered, washed with small amounts of isopropanol and n-heptane, and dried in vacuo to yield the product. Additional product was obtained by evaporation of the filtrate to dryness and purification of the remaining material via silica gel chromatography (eluent: n-Heptan/Ethylacetat), to yield a total amount of 6.4 g of the product.

MS (ESI+) m/z=413.9 [M+H]$^+$ 25.4 (3aS,6aS)-ethyl-1-(3-(3-fluorophenylsulfonyl)quinolin-8-yl)hexahydropyrrolo[3,4-b]pyrrole-5(1H)-carboxylate 0.255 of g 3-(3-fluorophenylsulfonyl)-8-iodoquinoline (0.617 mmol), 0.114 g of (3aS,6aS)-ethyl hexahydropyrrolo[3,4-b]pyrrole-5(1H)-carboxylate (0.617 mmol), 0.404 g of cesium carbonate (1.234 mmol), 0.014 g of palladium acetate (0.062 mmol) and 0.029 g of X-Phos (2-dicyclohexylphosphino-2',4',6'-triisopropylbiphenyl, 0.062 mmol) in 5 mL toluene were stirred at 90° C. for 8 h. The reaction mixture was directly purified via silica gel chromatography (eluent toluene/methanol 10/1+2.5% triethylamine). Fractions containing the product were combined and the solvent was evaporated to yield 0.271 g of the desired product which was used in example 26 without additional purification.

MS (ESI+) m/z=470.1 [M+H]$^+$

Example 26

3-(3-Fluoro-benzenesulfonyl)-8-(3aS,6aS)-hexahydropyrrolo[3,4-b]pyrrol-1-yl-quinoline hydrochloride A solution of 0.264 g of (3aS,6aS)-ethyl 1-(3-(3-fluorophenylsulfonyl)quinolin-8-yl)hexahydropyrrolo[3,4-b]pyrrole-5(1H)-carboxylate (0.562 mmol) and 0.338 g trimethylsilyl iodide (1.687 mmol) was stirred at reflux in chloroform (5 mL) for 1.5 h and additionally at room temperature for 16 h. Additional trimethylsilyl iodide was added and the reaction mixture was stirred at reflux for 6 h. The mixture was cooled to room temperature. Then, 0.27 g of methanol (8.43 mmol) were added with stirring and stirring was continued for 30 min. The solvent was evaporated, the remaining material was treated with water and the pH was adjusted to alkaline pH with concentrated aqueous ammonia. The aqueous layer was extracted three times with dichloromethane and the combined organic layers were dried over magnesium sulfate, filtered, and concentrated. The crude product was purified via silica gel chromatography and preparative HPLC. The hydrochloride salt was obtained by adding 2 N HCl in diethylether to a solution of the free base in tetrahydrofurane/diethyl ether. Thereby, a precipitate formed, which was filtered, washed with diethyl ether and dried in vacuo to yield 10 mg of the product.

MS (ESI+) m/z=398.1 [M+H]$^+$

Example 27

(1S,5R)-tert-butyl 3-(3-(3-fluorophenylsulfonyl)quinolin-8-yl)-3,6-diazabicyclo[3.2.0]heptane-6-carboxylate 0.153 g of (1S,5R)-tert-butyl 3-(3-(3-fluorophenylsulfonyl)quinolin-8-yl)-3,6-diazabicyclo[3.2.0]heptane-6-carboxylate were prepared by analogy to the method of Example 25.4 by coupling of 3-(3-fluorophenylsulfonyl)-8-iodoquinoline and (1S,5R)-tert-butyl 3,6-diazabicyclo[3.2.0]heptane-6-carboxylate.

MS (ESI+) m/z=484.2 [M+H]$^+$

Example 28

8-(1R,5R)-3,6-Diaza-bicyclo[3.2.0]hept-3-yl-3-(3-fluoro-benzenesulfonyl)-quinoline hydrochloride 0.150 g of (1S,5R)-tert-butyl 3-(3-(3-fluorophenylsulfonyl)quinolin-8-yl)-3,6-diazabicyclo[3.2.0]heptane-6-carboxylate from Example 27 were dissolved in 5 ml of ethanol. 5 mL 5N HCl in isopropanol was added and the mixture was stirred at room temperature for 16 h. The reaction mixture was concentrated and the residue was dissolved in small amounts of ethanol and precipitated with addition of diethyl ether. Recrystallization from ethanol/isopropanol (2:1) yielded 0.0275 g of the product.

MS (ESI+) m/z=384.1 [M+H]$^+$

Example 29

3-(3-Fluoro-benzenesulfonyl)-8-(hexahydro-pyrrolo[3,4-b]pyrrol-5-yl)-quinoline hydrochloride 0.088 g of 5-(3-(3-fluorophenylsulfonyl)quinolin-8-yl)octahydropyrrolo[3,4-b]pyrrol-1-ium chloride were prepared by analogy to the methods of Examples 27 and 28 by coupling of 3-(3-fluorophenylsulfonyl)-8-iodoquinoline with 1-(tert-butoxycarbonyl)-octahydropyrrolo[2,3-c]pyrrol-5-ium chloride and subsequent deprotection of the tert-butyl-oxycarbonyl derivative with HCl in isoproanol.

MS (ESI+) m/z=398.1 [M+H]$^+$

Example 30

3-(3-Fluoro-benzenesulfonyl)-8-(3aR,6aS)-hexahydro-pyrrolo[3,4-c]pyrrol-2-yl-quinoline hydrochloride 0.145 g of 3-(3-Fluoro-benzenesulfonyl)-8-(3aR,6aS)-hexahydro-pyrrolo[3,4-c]pyrrol-2-yl-quinoline hydrochloride were prepared by analogy to the methods of Examples 27 and 28 by coupling of 3-(3-fluorophenylsulfonyl)-8-iodoquinoline with commercially available (3aR,6aS)-Hexahydro-pyrrolo[3,4-c]pyrrole-2-carboxylic acid tert-butyl ester and subsequent deprotection of the tert-butyl-oxycarbonyl derivative with HCl in isoproanol.

MS (ESI+) m/z=398.1 [M+H]$^+$

Example 31

6-(3-(3-fluorophenylsulfonyl)quinolin-8-yl)octahydro-1H-pyrrolo[3,4-b]pyridin-1-ium chloride 0.073 g of 6-(3-(3-fluorophenylsulfonyl)quinolin-8-yl)octahydro-1H-pyrrolo[3,4-b]pyridin-1-ium chloride were prepared by analogy to the methods of Examples 27 and 28 by coupling of 3-(3-fluorophenylsulfonyl)-8-iodoquinoline with commercially available octahydro-pyrrolo[3,4-b]pyridine-6-carboxylic acid tert-butyl ester and subsequent deprotection of the tert-butyl-oxycarbonyl derivative with HCl in isoproanol.

MS (ESI+) m/z=412.2 [M+H]$^+$

Example 32

(1S,5S)-3-(3-(3-fluorophenylsulfonyl)quinolin-8-yl)-3-aza-6-azoniabicyclo[3.2.0]heptane hydrochloride 0.081 g of (1S,5S)-3-(3-(3-fluorophenylsulfonyl)quinolin-8-yl)-3-aza-6-azoniabicyclo[3.2.0]heptane hydrochloride were prepared by analogy to the methods of Examples 27 and 28 by coupling of 3-(3-fluorophenylsulfonyl)-8-iodoquinoline with (1R,5S)-tert-butyl 3,6-diazabicyclo[3.2.0]heptane-6-carboxylate and subsequent deprotection of the tert-butyl-oxycarbonyl derivative with HCl in isopropanol.

MS (ESI+) m/z=384.1 [M+H]$^+$

Example 33

5-(3-(3-fluorophenylsulfonyl)quinolin-8-yl)octahydro-1H-pyrrolo[3,4-c]pyridin-2-ium chloride 0.072 g of 5-(3-(3-fluorophenylsulfonyl)quinolin-8-yl)octahydro-1H-pyrrolo[3,4-c]pyridin-2-ium chloride were prepared by analogy to the methods of Examples 27 and 28 by coupling of 3-(3-fluorophenylsulfonyl)-8-iodoquinoline with commercially available tert-butyl hexahydro-1H-pyrrolo[3,4-c]pyridine-2(3H)-carboxylate and subsequent deprotection of the tert-butyl-oxycarbonyl derivative with HCl in isoproanol.

MS (ESI+) m/z=412.2 [M+H]$^+$

Example 34

8-(5-benzyl-1H-pyrrolo[3,4-c]pyridin-2(3H,3aH,4H,5H,6H,7H,7aH)-yl)-3-(3-fluorophenylsulfonyl)quinoline 34.1 tert-butyl 5-benzylhexahydro-1H-pyrrolo[3,4-c]pyridine-2(3H)-carboxylate 0.777 g of benzylbromide (4.54 mmol) were added dropwise to a mixture of 1.028 g of commercially available tert-butyl hexahydro-1H-pyrrolo[3,4-c]pyridine-2(3H)-carboxylate (4.54 mmol), 1.883 g potassium carbonate (13.62 mmol) and a spatula tip of 18-crown-6 in 25 ml of tetrahydrofurane. The reaction mixture was stirred for 16 h at room temperature, filtered and the filtrate was concentrated. The residue was dissolved in dichloromethane, the organic layer was washed with water, dried over magnesium sulfate, filtered and concentrated to yield 1.413 g of product that was used in the subsequent step without further purification.

MS (ESI+) m/z=317.2 [M+H]$^+$ 34.2 5-benzyloctahydro-1H-pyrrolo[3,4-c]pyridine-2,5-diium chloride 1.355 g of tert-butyl 5-benzylhexahydro-1H-pyrrolo[3,4-c]pyridine-2(3H)-carboxylate (4.28 mmol) were dissolved in 10 ml of ethanol. To the solution 20 ml of 5 N HCl in isopropanol were added and the obtained mixture was stirred at room temperature for 16 h. After addition of diethyl ether the product precipitated. The product was filtered and after an additional washing with diethyl ether, the product was dried. Additional product was obtained by concentration of the filtrates and crystallization from diethyl ether. Combined amounts of product were 1.07 g.

MS (ESI+) m/z=217.2 [M+H]$^+$ 34.3 8-(5-benzyl-1H-pyrrolo[3,4-c]pyridin-2(3H,3aH,4H,5H,6H,7H,7aH)-yl)-3-(3-fluorophenylsulfonyl)quinoline 0.367 g of 8-(5-benzyl-1H-pyrrolo[3,4-c]pyridin-2(3H,3aH,4H,5H,6H,7H,7aH)-yl)-3-(3-fluorophenylsulfonyl)quinoline were prepared by analogy to the method of Example 27 by coupling of 3-(3-fluorophenylsulfonyl)-8-iodoquinoline with 5-benzyloctahydro-1H-pyrrolo[3,4-c]pyridine-2,5-diium chloride MS (ESI+) m/z=502.2 [M+H]$^+$ Example 35

3-(3-Fluoro-benzenesulfonyl)-8-(octahydro-pyrrolo[3,4-c]pyridin-2-yl)-quinoline hydrochloride A suspension of 0.05 g Pd/C (10%) in 1 ml of water was added to a solution of 0.331 g of 8-(5-benzyl-1H-pyrrolo[3,4-c]pyridin-2(3H,3aH,4H,5H,6H,7H,7aH)-yl)-3-(3-fluorophenylsulfonyl)quinoline (0.66 mmol) in 10 ml of ethanol. The mixture was beate to 80° C. Then 0.41 g of ammonium formiate (6.61 mmol) in 2 ml of water were added. After 1 h at 80° C., additional catalyst and ammonium formiate were added. Stirring was continued for 1 h at 80° C. Then the catalyst was filtered off and the filtrate was concentrated. The residue was partitioned between dichloromethane and water. The aqueous layer was extracted twice with dichloromethane. The combined organic layers were dried over magnesium sulfate, filtered and concentrated. The crude product was purified via silica gel chromatography (eluent: toluene/methanol 10/1+2.5% triethylamine, Analogix SF 15/24 g). Fractions containing the product were combined, concentrated and the hydrochloride was formed by addition of HCl in diethylether. 0.018 g of product were obtained.

MS (ESI+) m/z=412.2 [M+H]$^+$

Example 36

8-((3aS,6aS)-1-benzylhexahydropyrrolo[3,4-b]pyrrol-5(1H)-yl)-3-(3-fluorophenylsulfonyl)quinoline 0.157 g of 8-((3aS,6aS)-1-benzylhexahydropyrrolo[3,4-b]pyrrol-5(1H)-yl)-3-(3-fluorophenylsulfonyl)quinoline were prepared by analogy to the method of Example 27 by coupling of 3-(3-fluorophenylsulfonyl)-8-iodoquinoline with (3aS,6aS)-1-benzyloctahydropyrrolo[3,4-b]pyrrole MS (ESI+) m/z=488.2 [M+H]$^+$ Example 37

3-(3-Fluoro-benzenesulfonyl)-8-((3aR,6aS)-5-methyl-hexahydropyrrolo[3,4-c]pyrrol-2-yl)-quinoline hydrochloride 0.05 g of 3-(3-Fluoro-benzenesulfonyl)-8-((3aR,6aS)-hexahydro-pyrrolo[3,4-c]pyrrol-2-yl)-quinoline hydrochloride (0.117 mmol) were dissolved in methanol. 1 Equivalent of sodium hydroxide in methanol was added, and the mixture was concentrated. The residue was dissolved in 5 ml of dichloromethane and 0.007 g of acetic acid (0.117 mmol), 8.7 µl of aqueous formaldehyde solution (0.117 mmol) and 0.025 g of sodium triacetoxyborohydride (0.117 mmol) were subsequently added. After completion of the reaction, dichloromethane was added. The organic layer was washed with aqueous sodium bicarbonate solution, and the aqueous layer was reextracted twice with dichloromethane. The combined organic layers were dried over magnesium sulfate, filtered, and concentrated. The residue was dissolved in tetrahydrofurane and the hydrochloride salt was formed by addition of HCl in diethyl ether. After filtration, the product was washed with diethyl ether and dried in vacuo (0.033 g of product formed).

MS (ESI+) m/z=412.2 [M+H]$^+$

Example 38

5-(3-(4-fluorophenylsulfonyl)quinolin-8-yl)octahydropyrrolo[3,4-c]pyrrol-2-ium chloride 0.045 g of 5-(3-(4-fluorophenylsulfonyl)quinolin-8-yl)octahydropyrrolo[3,4-c]pyrrol-2-ium chloride were prepared by analogy to the methods of Examples 27 and 28 by coupling of 3-(3-fluorophenylsulfonyl)-8-iodoquinoline with commercially available (3aR,6aS)-hexahydro-pyrrolo[3,4-c]pyrrole-2-carboxylic acid tert-butyl ester and subsequent deprotection of the tert-butyl-oxycarbonyl derivative with HCl in isoproanol.

MS (ESI+) m/z=398.2 [M+H]$^+$

The compounds of examples 39 to 44 were prepared by analogy to the methods of Examples 1 to 38.

Example 39

3-(4-fluorophenylsulfonyl)-8-(hexahydropyrrolo[3,4-b]pyrrol-5(1H)-yl)quinoline

MS (ESI+) m/z=398.2 [M+H]$^+$

Example 40

8-(5-benzylhexahydropyrrolo[3,4-c]pyrrol-2(1H)-yl)-3-(phenylsulfonyl)-quinoline

MS (ESI+) m/z=470.2 [M+H]$^+$

Example 41

8-(5-methyl-1H-pyrrolo[3,4-c]pyridin-2(3H,3aH,4H,5H,6H,7H,7aH)-yl)-3

Example 42

2-(3-(phenylsulfonyl)quinolin-8-yl)dodecahydro-1H-pyrido[4,3-b]indole

MS (ESI+) m/z=448.1 [M+H]$^+$

Example 43

8-(hexahydropyrrolo[3,4-c]pyrrol-2(1H)-yl)-3-(phenylsulfonyl)quinoline

MS (ESI+) m/z=380.1 [M+H]$^+$

Example 44

8-(1H-pyrrolo[3,4-c]pyridin-2(3H,3aH,4H,5H,6H,7H,7aH)-yl)-3-(3-(trifluoromethyl)phenylsulfonyl)quinoline MS (ESI+) m/z=462.2 [M+H]$^+$ II. Biological Investigations Displacement of Radioligands Binding to the Following Cloned Human Receptors
1. Preparation of Membranes by Ultrasonic Treatment and Differential Centrifugation Cells from stable clonal cell lines expressing the corresponding receptor (5-HT$_6$, $\alpha_1$-adrenergic, dopamine D$_2$ or histamine H$_1$ receptors) were washed with PBS (w/o Ca$^{++}$, Mg$^{++}$) and harvested in PBS with 0.02% EDTA. The cells were collected by centrifugation at 500 g for 10 min. at 4° C., washed with PBS and centrifuged (500 g, 10 min. 4° C.). The pellets were stored at −80° C. until use. For membrane preparation, the thawed cell pellet was resuspended in ice-cold sucrose buffer (0.25 M sucrose, 10 mM Hepes (pH 7.4), 1 mM Phenylmethylsulfonyl fluoride (PMSF) in DMSO, 5 µg/ml Pepstatin-A, 3 mM EDTA, 0.025% Bacitracin) and homogenized with a Branson Sonifier W-250 (Settings: Timer 4; Output Control 3; Duty Cycle constant; 2 to 3 cycles). Cell disruption was checked with the aid of a microscope. Remaining unbroken cells were pelleted at 1.000 g for 10 min. at 4° C. The sucrose buffer supernatant was then centrifuged at 60.000 g for 1 h at 4° C. (Beckman Ultrazentrifuge XL 80). The pellet was resuspended in 30 ml ice-cold Tris buffer (20 mM TRIS (pH 7.4), 5 µg/ml Pepstatin A, 0.1 mM PMSF, 3 mM EDTA) by pipetting through a 10 ml serological pipet and centrifuged for 1 h at 4° C. at 60.000 g. A final resuspension was performed in a small volume of ice-cold Tris buffer (see above) by pressing through a serological pipet followed by ultrasonic treatment with a Branson Sonifier W-250 (Settings: Timer 1; Output Control 3; Duty Cycle constant; 1 cycle). Protein concentration was determined (BCA-Kit; Pierce) and aliquots stored at −80° C. or in liquid nitrogen for long-term storage.

2. Receptor Binding Experiments

All receptor binding experiments were carried out in the corresponding assay buffer in a total volume of 200 µl in the presence of various concentrations of test compound (10$^{-5}$ M to 10$^{-9}$ M, tenfold serial dilution, duplicate determinations). The assays were terminated by filtration on polyethylenimine (PEI 0.1% or 0.3%) presoaked Packard Unifilter Plates (GF/C or GF/B) with a Tomtec MachIII U 96well-plate harvester. After the plates had been dried for 2 h at 55° C. in a drying chamber scintillation cocktail (BetaPlate Scint; PerkinElmer) was added. Radioactivity was measured in a Microbeta Trilux two hours after the addition of the scintillation mixture. Data derived from liquid scintillation counting were analysed by iterative non-linear regression analysis with the use of the Statistical Analysis System (SAS): a program similar to "LIGAND" as described by Munson and Rodbard (Analytical Biochemistry 107, 220-239 (1980).

a) 5-HT$_6$ Receptor Binding Assay

HEK293 cells stably expressing the h-5-HT$_6$ receptor (NCBI Reference Sequence XM 001435) were cultured in RPMI1640 medium supplemented with 25 mM HEPES, 10% fetal calf serum and 1-2 mM glutamine. The membrane preparation was performed as described in section 1. For these membranes a K$_D$ of 1.95 nM for [$^3$H]-LSD (Lysergic Acid Diethylamide; Amersham, TRK1038) was determined by means of saturation binding experiments. On the day of the assay, the membranes were thawed, diluted in assay buffer (50 mM Tris-HCl, 5 mM $CaCl_2$, 0.1% ascorbic acid, 10 μM pargyline, pH 7.4) to a concentration of 8 μg protein/assay and homogenized by gentle vortexing For inhibition studies, in M [$^3$H]-Lysergic Acid Diethylamide was incubated in the presence of various concentrations of test compound in assay buffer. Non-specific binding was defined with 1 μM methiothepin. The binding reaction was carried out for 3.5 h at room temperature. During the incubation, the plates were shaken on a plate shaker at 100 rpm and terminated by filtration on Packard Unifilter GF/C (0.1% PEI) plates, followed by 2 wash cycles with ice-cold 50 mM Tris-HCl, 5 mM $CaCl_2$.

a) Dopamine $D_2$ Receptor Binding Assay

HEK293 cells stably expressing the dopamine $D_2$ receptor (NCBI Reference Sequence NM_000795) were cultured in RPMI1640 medium supplemented with 25 mM HEPES, 10% fetal calf serum and 1-2 mM glutamine. The membrane preparation was performed as described in section 1. For these membranes a $K_D$ of 0.22 nM for [$^{125}$I]-iodospiperone (Perkin Elmer Life Sciences, NEX284) was determined by means of saturation binding experiments. On the day of the assay, the membranes were thawed, diluted in assay buffer (50 mM Tris-HCl, 120 mM NaCl, 5 mM $MgCl_2$, 5 mM KCl, 1.5 mM $CaCl_2$, pH 7.4) to a concentration of 15 μg protein/ assay and homogenized by gentle vortexing. For inhibition studies, 0.01 nM [$^{125}$I]-iodospiperone (PerkinElmer Life Sciences, NEX284) was incubated in the presence of various concentrations of test compound in assay buffer. Non-specific binding was defined with 1 μM haloperidol. The binding reaction was carried out for 1 h at room temperature and terminated by filtration on Packard Unifilter GF/B (0.1% PEI) plates, followed by 6 wash cycles with an ice-cold 7% polyethylenglycol solution.

b) $α_1$-Adrenergic Receptor Binding Assay

CHO-$K_1$ cells stably expressing the $α_1$-adrenergic receptor (NCBI Reference Sequence NM_033303) were cultured in RPMI1640 medium supplemented with 25 mM HEPES, 10% fetal calf serum and 1-2 mM glutamine. The membrane preparation was performed as described in section 1. For these membranes a $K_D$ of 0.12 nM for [$^3$H]-prazosine (PerkinElmer Life Sciences, NET823) was determined by means of saturation binding experiments. On the day of the assay, the membranes were thawed, diluted in assay buffer (50 mM Tris-HCl, pH 7.4) to a concentration of 4 μg protein/assay and homogenized by gentle vortexing. For inhibition studies, 0.1 nM [$^3$H]-prazosine (PerkinElmer Life Sciences, NET823) was incubated in the presence of various concentrations of test compound in assay buffer. Non-specific binding was defined with 1 μM phentolamine. The binding reaction was carried out for 1 h at room temperature and terminated by filtration on Packard Unifilter GF/C (0.1% PEI) plates, followed by 3 wash cycles with ice-cold assay buffer.

c) $H_1$ Receptor Binding Assay

CHO-$K_1$ cells stably expressing the histamine $H_1$ receptor (Euroscreen-ES-390-C, NCBI Reference Sequence NM_000861) were cultured in RPMI1640 medium supplemented with 25 mM HEPES, 10% fetal calf serum and 1-2 mM glutamine. The membrane preparation was performed as described in section 1. For these membranes a $K_D$ of 0.83 nM for [$^3$H]-pyrilamine (PerkinElmer Life Sciences, NET594) was determined by means of saturation binding experiments. On the day of the assay, the membranes were thawed, diluted in assay buffer (50 mM $Na_2HPO_4$, 50 mM $KH_2PO_4$, pH 7.4) to a concentration of 6 μg protein/assay and homogenized by gentle vortexing. For inhibition studies, 1 nM [$^3$H]-pyrilamine (PerkinElmer Life Sciences, NET594) was incubated in the presence of various concentrations of test compound in assay buffer. Non-specific binding was defined with 1 μM pyrilamine. The binding reaction was carried out for 50 minutes at room temperature and terminated by filtration on Packard Unifilter GF/C (0.3% PEI) plates, followed by 2 wash cycles with ice-cold assay buffer.

3. Data Analysis

Data derived from liquid scintillation counting were analyzed by iterative non-linear regression analysis with the use of the Statistical Analysis System (SAS): a program similar to "LIGAND" as described by Munson and Rodbard (Anal. Biochem. 1980, 107, 220-239). Fitting was performed according to formulae described by Feldman (Anal. Biochem. 1972, 48, 317-338). $IC_{50}$, nH and $K_i$ values were expressed as geometrical mean. For receptors with a low affinity for the test compound, where the highest tested compound concentration inhibited less than 30% of specific radioligand binding, $K_i$-values were determined according to the equation of Cheng and Prusoff (Biochem. Pharmacol. 1973, 22, 2099-2108) and expressed as greater than (>).

The results of the receptor binding studies are expressed as receptor binding constants $K_i$(5-$HT_6$), $K_i$($D_2$), $K_i$($α_1$-adrenergic) and $K_i$($H_1$), respectively, as described herein before, and given in table I.

In these tests, the compounds according to the invention exhibit very good affinities for the 5-$HT_6$ receptor ($K_i$<250 nM or <50 nM or <20 nM or <10 nM and frequently <5 nM or <1 nM). Furthermore those compounds bind selectively to the 5-$HT_6$ receptor, as compared to the affinity for the $D_2$, the $α_1$-adrenergic or the $H_1$ receptors. These compounds exhibit little affinities for the $D_2$, $α_1$-adrenergic or $H_1$ receptors ($K_i$>250 nM or >1000 nM and frequently >10000 nM).

TABLE I

| Example | $K_i$(5-$HT_6$) |
|---|---|
| 1 | +++ |
| 2 | + |
| 3 | + |
| 4 | +++ |
| 10 | + |
| 12 | +++ |
| 13 | +++ |
| 14 | +++ |
| 15 | ++ |
| 16 | +++ |
| 18 | +++ |
| 19 | ++ |
| 20 | +++ |
| 22 | +++ |
| 24 | +++ |
| 26 | +++ |
| 28 | +++ |
| 29 | +++ |
| 30 | +++ |
| 31 | +++ |
| 32 | +++ |
| 39 | +++ |
| 40 | +++ |
| 41 | ++ |
| 42 | + |
| 43 | +++ |
| 44 | +++ |

In table I "n.d." means not determined; "+++" ≙ $K_i$ < 10 nM; "++" ≙ $K_i$ < 50 nM; "+" ≙ $K_i$ < 250 nM; "−" ≙ $K_i$ > 250 nM; "−−" ≙ $K_i$ > 1000; "−−−" ≙ $K_i$ > 10000 nM.

We claim:

1. A method for treating a cognitive dysfunction associated with Alzheimer's disease, a cognitive dysfunction associated with schizophrenia, or obesity, said method comprising administering an effective amount of the compound of formula (I) or a physiologically tolerated acid addition salt or a N-oxide thereof to a subject in need thereof
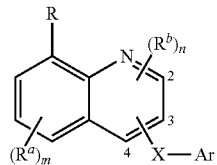
(I)
where in formula (I)
R is a radical selected from the group consisting of
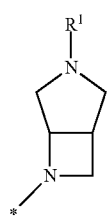 R-1
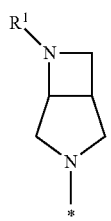 R-5
 R-11
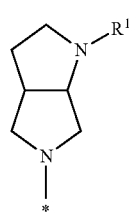 R-12
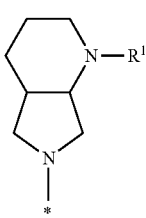 R-15
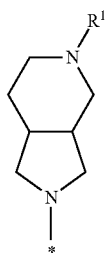 R-16
 R-26
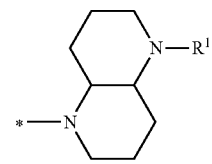 R-38
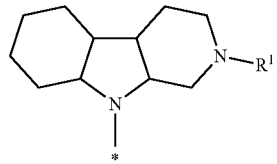 R-39
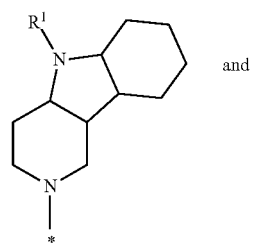 R-41
and
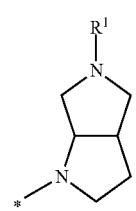 R-44

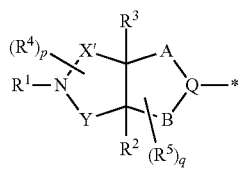

wherein * indicates the binding site to the quinolinyl radical;
$R^1$ is hydrogen, $C_1$-$C_6$-alkyl, $C_1$-$C_6$-hydroxyalkyl, $C_1$-$C_6$-haloalkyl, $C_1$-$C_6$-alkoxy-$C_1$-$C_4$-alkyl, $C_1$-$C_6$-haloalkoxy-$C_1$-$C_4$-alkyl, $C_3$-$C_6$-cycloalkyl, $C_3$-$C_6$-halocycloalkyl, $C_3$-$C_6$-cycloalkyl-$C_1$-$C_4$-alkyl, aryl-$C_1$-$C_4$-alkyl, hetaryl-$C_1$-$C_4$-alkyl, $C_3$-$C_6$-alkenyl, $C_3$-$C_6$-haloalkenyl, formyl, $C_1$-$C_4$-alkylcarbonyl, $C_1$-$C_4$-alkoxycarbonyl, phenoxycarbonyl or benzyloxycarbonyl, where the phenyl rings in the last two mentioned moieties are unsubstituted or carry 1, 2 or 3 substituents, selected from halogen, $C_1$-$C_4$-alkyl or $C_1$-$C_4$-haloalkyl;
n is 0, 1 or 2;
m is 0, 1, 2 or 3;
$R^a$, $R^{ib}$ are independently selected from the group consisting of halogen, CN, $C_1$-$C_4$-alkyl, $C_1$-$C_4$-haloalkyl, $C_1$-$C_4$-alkoxy, $C_1$-$C_4$-haloalkoxy, $C(O)R^{aa}$, $C(O)NR^{cc}R^{bb}$ and $NR^{cc}R^{bb}$;
wherein $R^{aa}$ is hydrogen, $C_1$-$C_4$-alkyl, $C_1$-$C_4$-haloalkyl, $C_1$-$C_4$-alkoxy or $C_1$-$C_4$-haloalkoxy, and
$R^{cc}$, $R^{bb}$ are independently selected from the group consisting of hydrogen and $C_1$-$C_4$-alkyl;
X is $S(O)_2$; which is located in the 3- or 4-position of the quinoline ring;
Ar is phenyl, which is unsubstituted or may carry 1, 2, 3 substituents $R^x$, wherein
$R^x$ is halogen, CN, $NO_2$, $C_1$-$C_6$-alkyl, $C_1$-$C_6$-haloalkyl, $C_1$-$C_6$-hydroxyalkyl, $C_1$-$C_6$-alkoxy-$C_1$-$C_4$-alkyl, $C_2$-$C_6$-alkenyl, $C_2$-$C_6$-haloalkenyl, $C_3$-$C_6$-cyclo-alkyl, $C_3$-$C_6$-halocycloalkyl, $C_1$-$C_6$-alkoxy, $C_1$-$C_6$-hydroxyalkoxy, $C_1$-$C_6$-alkoxy-$C_1$-$C_4$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_1$-$C_6$-alkylcarbonyl, $C_1$-$C_6$-haloalkylcarbonyl, $C_1$-$C_6$-alkylcarbonylamino, $C_1$-$C_6$-haloalkyl-carbonylamino, carboxy, NH—C(O)—$NR^{x1}R^{x2}$, $NR^{x1}R^{x2}$, $NR^{x1}R^{x2}$—$C_1$-$C_6$-alkylene, O—$NR^{x1}R^{x2}$, wherein $R^{x1}$ and $R^{x2}$ in the last 4 mentioned radicals are independently of each other hydrogen, $C_1$-$C_6$-alkyl, $C_1$-$C_6$-haloalkyl or $C_1$-$C_6$-alkoxy or $R^{x1}$ and $R^{x2}$ in the last 4 mentioned radicals together with the nitrogen atom form an N-bound 5-, 6- or 7-membered, saturated heteromonocycle or an N-bound 7-, 8-, 9- or 10-membered, saturated heterobicycle which are unsubstituted or which carry 1, 2, 3 or 4 radicals selected from $C_1$-$C_4$-alkyl, $C_1$-$C_4$-haloalkyl, $C_1$-$C_4$-hydroxyalkyl and $C_1$-$C_4$-alkoxy and wherein 2 radicals $R^x$, which are bound to adjacent carbon atoms of Ar may form a saturated or unsaturated 5- or 6-membered carbocyclic or heterocyclic ring, which itself may carry a radical $R^x$.

2. The method of claim 1, wherein $R^1$ is hydrogen.
3. The method of claim 1, wherein X is located in the 3-position of the quinolinyl moiety.
4. The method of claim 1, wherein X is located in the 4-position of the quinolinyl moiety.
5. The method of claim 1, wherein $R^x$ is selected from the group consisting of halogen, CN, $C_1$-$C_4$-alkyl, $C_1$-$C_4$-haloalkyl, $C_1$-$C_4$-alkoxy, $C_1$-$C_4$-haloalkoxy, $C_3$-$C_6$-cycloalkyl and a group $NR^{x1}R^{x2}$.
6. The method of claim 1, wherein m is 0.
7. The method of claim 1, wherein n is 0.
8. The method of claim 1, where the compound of formula (I) is a compound of the formula (Ia.a)

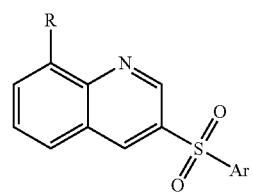

wherein R is a radical R-12 or R-16

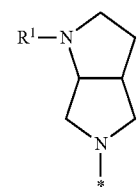

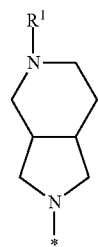

wherein $R^1$ is hydrogen and wherein Ar is as defined in claim 1.

9. The method of claim 8 where R in formula (Ia.a) is a radical of the formula R-16b,

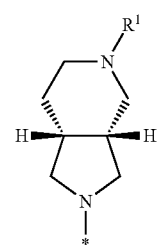

wherein $R^1$ is hydrogen.

10. The method of claim 1, where the compound of formula (I) is a compound of the formula (Ia.a)

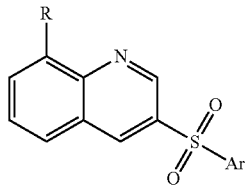

(Ia.a)

wherein m is 0, n is 0 and wherein R is a radical R-16b

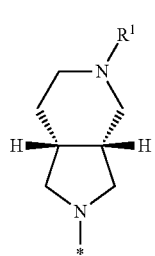

R-16b wherein $R^1$ is hydrogen or methyl and wherein Ar is selected from the group consisting of phenyl, 3-fluorophenyl, 4-fluorophenyl, 3-trifluoromethylphenyl, 3-trifluoromethoxyphenyl, 3-difluoromethylphenyl, 4-(oxazol-5-yl)phenyl, 3-(oxazol-2-yl)phenyl, 3-(oxazol-4-yl)phenyl and 3-(oxazol-5-yl)phenyl.

11. The method of claim 1, where the compound of formula (I) or a physiologically tolerated acid addition salt or a N-oxide thereof is administered as a pharmaceutical composition comprising the compound of formula (I) or a physiologically tolerated acid addition salt or a N-oxide thereof together with at least one physiologically acceptable carrier or auxiliary substance.

12. The method of claim 1, wherein $R^x$ is selected from the group consisting of halogen, $C_1$-$C_6$-alkyl, $C_1$-$C_6$-haloalkyl, $C_1$-$C_6$-hydroxyalkyl, $C_1$-$C_6$-alkoxy, $C_1$-$C_6$-alkoxy-$C_1$-$C_4$-alkyl, $C_1$-$C_6$-haloalkoxy, $C_2$-$C_6$-alkenyl, $C_2$-$C_6$-haloalkenyl and a group $NR^{x1}R^{x2}$.

13. The method of claim 1, wherein the compound of formula (I), or a physiologically tolerated acid addition salt or a N-oxide thereof, is selected from the group consisting of:
 8-(Hexahydropyrrolo[3,4-b]pyrrol-5(1H)-yl)-3-(phenylsulfonyl)quinoline;
 Benzyl 6-(3-(phenylsulfonyl)quinolin-8-yl)-3,6-diazabicyclo[3.2.0]heptane-3-carboxylate;
 tert-butyl 2-(3-(phenylsulfonyl)quinolin-8-yl)hexahydro-1H-pyrrolo[3,4-c]pyridine-5(6H)-carboxylate;
 3-(Phenylsulfonyl)-8-(1H-pyrrolo[3,4-c]pyridin-2(3H,3aH,4H,5H,6H,7H,7aH)-yl)quinoline;
 (1R,5S)-tert-butyl 3-(3-(phenylsulfonyl)quinolin-8-yl)-3,6-diazabicyclo[3.2.0]heptane-6-carboxylate;
 8-((1S,5S)-3,6-diazabicyclo[3.2.0]heptan-3-yl)-3-(phenylsulfonyl)quinoline;
 (3aS,6aS)-ethyl 1-(3-(phenylsulfonyl)quinolin-8-yl)hexahydropyrrolo[3,4-b]pyrrole-5(1H)-carboxylate;
 tert-butyl 5-(3-(4-fluorophenylsulfonyl)quinolin-8-yl)hexahydropyrrolo[3,4-b]pyrrole-1(2H)-carboxylate;
 tert-butyl 5-(3-(phenylsulfonyl)quinolin-8-yl)octahydro-1,5-naphthyridine-1(2H)-carboxylate;
 1-(3-(phenylsulfonyl)quinolin-8-yl)decahydro-1,5-naphthyridine;
 tert-butyl 2-(3-(4-fluorophenylsulfonyl)quinolin-8-yl)hexahydro-1H-pyrrolo[3,4-c]pyridine-5(6H)-carboxylate;
 8-((3aS,6aS)-hexahydropyrrolo[3,4-b]pyrrol-1(2H)-yl)-3-(phenylsulfonyl)quinoline;
 3-(4-fluorophenylsulfonyl)-8-(1H-pyrrolo[3,4-c]pyridin-2(3H,3aH,4H,5H,6H,7H,7aH)-yl)quinoline;
 3-(4-fluorophenylsulfonyl)-8-(hexahydropyrrolo[3,4-c]pyrrol-2(1H)-yl)quinoline;
 tert-butyl 5-(3-(3-(trifluoromethoxy)phenylsulfonyl)quinolin-8-yl)hexahydropyrrolo[3,4-c]pyrrole-2(1H)-carboxylate;
 8-(hexahydropyrrolo[3,4-c]pyrrol-2(1H)-yl)-3-(3-(trifluoromethoxy)phenylsulfonyl)quinoline;
 tert-butyl 5-(3-(3-(5-(tert-butoxycarbonyl)hexahydropyrrolo[3,4-c]pyrrol-2(1H)-yl)phenylsulfonyl)quinolin-8-yl)hexahydropyrrolo[3,4-c]pyrrole-2(1H)-carboxylate;
 8-(hexahydropyrrolo[3,4-c]pyrrol-2(1H)-yl)-3-(3-(hexahydropyrrolo[3,4-c]pyrrol-2(1H)-yl)phenylsulfonyl)quinoline;
 tert-butyl 2-(3-(3-(trifluoromethoxy)phenylsulfonyl)quinolin-8-yl)hexahydro-1H-pyrrolo[3,4-c]pyridine-5(6H)-carboxylate;
 8-(1H-pyrrolo[3,4-c]pyridin-2(3H,3aH,4H,5H,6H,7H,7aH)-yl)-3-(3-(trifluoromethoxy)phenylsulfonyl)quinoline;
 tert-butyl 5-(3-(3-(trifluoromethyl)phenylsulfonyl)quinolin-8-yl)hexahydropyrrolo[3,4-b]pyrrole-1(2H)-carboxylate;
 8-(hexahydropyrrolo[3,4-b]pyrrol-5(1H)-yl)-3-(3-(trifluoromethyl)phenylsulfonyl)quinoline;
 (3aR,6aS)-tert-butyl 5-(3-(3-(trifluoromethyl)phenylsulfonyl)quinolin-8-yl)hexahydropyrrolo[3,4-c]pyrrole-2(1H)-carboxylate;
 8-((3aR,6aS)-hexahydropyrrolo[3,4-c]pyrrol-2(1H)-yl)-3-(3-(trifluoromethyl)phenylsulfonyl)quinoline;
 (3aS,6aS)-ethyl-1-(3-(3-fluorophenylsulfonyl)quinolin-8-yl)hexahydropyrrolo[3,4-b]pyrrole-5(1H)-carboxylate;
 3-(3-Fluoro-benzenesulfonyl)-8-(3aS,6aS)-hexahydropyrrolo[3,4-b]pyrrol-1-yl-quinoline;
 (1S,5R)-tert-butyl 3-(3-(3-fluorophenylsulfonyl)quinolin-8-yl)-3,6-diazabicyclo[3.2.0]heptane-6-carboxylate;
 8-(1R,5R)-3,6-Diaza-bicyclo[3.2.0]hept-3-yl-3-(3-fluoro-benzenesulfonyl)-quinoline;
 3-(3-Fluoro-benzenesulfonyl)-8-(hexahydro-pyrrolo[3,4-b]pyrrol-5-yl)-quinoline;
 3-(3-Fluoro-benzenesulfonyl)-8-(3aR,6aS)-hexahydropyrrolo[3,4-c]pyrrol-2-yl-quinoline;
 3-(3-fluorophenylsulfonyl)-8-(tetrahydro-1H-pyrrolo[3,4-b]pyridin-6(2H,7H,7aH)-yl)quinoline;
 8-((1S,5S)-3,6-diazabicyclo[3.2.0]heptan-3-yl)-3-(3-fluorophenylsulfonyl)quinoline;
 5-(3-(3-fluorophenylsulfonyl)quinolin-8-yl)octahydro-1H-pyrrolo[3,4-c]pyridin-2-ium chloride;
 8-(5-benzyl-1H-pyrrolo[3,4-c]pyridin-2(3H,3aH,4H,5H,6H,7H,7aH)-yl)-3-(3-fluorophenylsulfonyl)quinoline;
 3-(3-Fluoro-benzenesulfonyl)-8-(octahydro-pyrrolo[3,4-c]pyridin-2-yl)-quinoline;
 8-((3aS,6aS)-1-benzyl hexahydropyrrolo[3,4-b]pyrrol-5(1H)-yl)-3-(3-fluorophenylsulfonyl)quinoline;
 3-(3-Fluoro-benzenesulfonyl)-8-((3aR,6aS)-5-methyl-hexahydropyrrolo[3,4-c]pyrrol-2-yl)-quinoline;

3-(4-fluorophenylsulfonyl)-8-(hexahydropyrrolo[3,4-c] pyrrol-2(1H)-yl)quinoline;

3-(4-fluorophenylsulfonyl)-8-(hexahydropyrrolo[3,4-b] pyrrol-5(1H)-yl)quinoline;

8-(5-benzylhexahydropyrrolo[3,4-c]pyrrol-2(1H)-yl)-3-(phenylsulfonyl)-quinoline;

8-(5-methyl-1H-pyrrolo[3,4-c]pyridin-2(3H,3aH,4H,5H,6H,7H,7aH)-yl)-3-(phenylsulfonyl)quinoline;

2-(3-(phenylsulfonyl)quinolin-8-yl)dodecahydro-1H-pyrido[4,3-b]indole;

8-(hexahydropyrrolo[3,4-c]pyrrol-2(1H)-yl)-3-(phenylsulfonyl)quinoline; and 8-(1H-pyrrolo[3,4-c]pyridin-2(3H,3aH,4H,5H,6H,7H,7aH)-yl)-3-(3-(trifluoromethyl)phenylsulfonyl)quinolone.

* * * * *

UNITED STATES PATENT AND TRADEMARK OFFICE
CERTIFICATE OF CORRECTION

PATENT NO. : 8,440,694 B2  
APPLICATION NO. : 13/613344  
DATED : May 14, 2013  
INVENTOR(S) : Sean Colm Turner et al.

Page 1 of 1

It is certified that error appears in the above-identified patent and that said Letters Patent is hereby corrected as shown below:

In the Claims section, on Column 59, Line 1, please delete the following:

"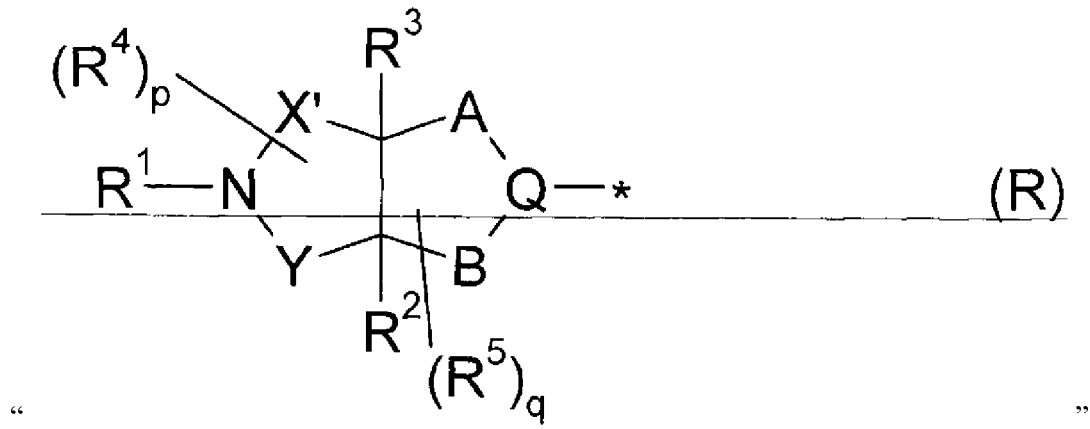"

Signed and Sealed this  
Twenty-fifth Day of June, 2013

Teresa Stanek Rea  
*Acting Director of the United States Patent and Trademark Office*